(12) United States Patent
Glinka et al.

(10) Patent No.: US 8,119,667 B2
(45) Date of Patent: *Feb. 21, 2012

(54) CARBONATES OF FENICOL ANTIBIOTICS

(75) Inventors: Tomasz W. Glinka, Cupertino, CA (US); Dale Edward Shuster, South Orange, NJ (US); Chander Shekher Celly, Colonia, NJ (US); Robert D. Simmons, Martinsville, NJ (US); Jason Zhang, Foster City, CA (US)

(73) Assignee: Schering-Plough Animal Health Corporation, Summit, NJ (US)

( * ) Notice: Subject to any disclaimer, the term of this patent is extended or adjusted under 35 U.S.C. 154(b) by 1276 days.

This patent is subject to a terminal disclaimer.

(21) Appl. No.: 11/611,997

(22) Filed: Dec. 18, 2006

(65) Prior Publication Data

US 2007/0155799 A1 Jul. 5, 2007

Related U.S. Application Data

(60) Provisional application No. 60/754,967, filed on Dec. 29, 2005, provisional application No. 60/781,487, filed on Mar. 10, 2006.

(51) Int. Cl.
| *A61K 31/44* | (2006.01) |
| *A61K 31/41* | (2006.01) |
| *A61K 31/42* | (2006.01) |
| *A61K 31/265* | (2006.01) |
| *C07D 211/78* | (2006.01) |
| *C07D 285/12* | (2006.01) |
| *C07D 261/06* | (2006.01) |
| *C07C 69/96* | (2006.01) |

(52) U.S. Cl. ........ 514/344; 514/362; 514/378; 514/512; 546/286; 548/138; 548/247; 558/273

(58) Field of Classification Search .................. 514/378, 514/512, 344, 362; 546/286; 548/138, 247; 558/273
See application file for complete search history.

(56) References Cited

U.S. PATENT DOCUMENTS

| 2,776,992 A | 1/1957 | Gregory |
| 3,183,265 A | 5/1965 | von Strandtmann et al. |
| 3,950,360 A | 4/1976 | Aoki et al. |
| 3,984,564 A | 10/1976 | Aoki et al. |
| 4,199,569 A | 4/1980 | Chabala et al. |
| 4,235,892 A | 11/1980 | Nagabhushan |
| 4,310,519 A | 1/1982 | Albers-Schonberg et al. |
| 4,311,857 A | 1/1982 | Nagabhushan et al. |
| 4,361,557 A | 11/1982 | Nagabhushan et al. |
| 4,582,918 A | 4/1986 | Nagabhushan et al. |
| 4,743,700 A | 5/1988 | Jommi et al. |
| 4,820,695 A | 4/1989 | Debono et al. |
| 4,876,352 A | 10/1989 | Schumacher et al. |
| 4,918,095 A | 4/1990 | Della Bella et al. |
| 4,973,750 A | 11/1990 | Nagabhushan et al. |
| 5,082,863 A | 1/1992 | Apelian et al. |
| 5,089,480 A | 2/1992 | Gibson et al. |
| 5,105,009 A | 4/1992 | Jommi et al. |
| 5,153,328 A | 10/1992 | Jommi et al. |
| 5,227,494 A | 7/1993 | Schumacher et al. |
| 5,243,056 A | 9/1993 | Jommi et al. |
| 5,288,710 A | 2/1994 | Cvetovich |
| 5,332,835 A | 7/1994 | Jommi et al. |
| 5,352,832 A | 10/1994 | Wu et al. |
| 5,382,673 A | 1/1995 | Clark et al. |
| 5,399,717 A | 3/1995 | Cvetovich et al. |
| 5,567,844 A | 10/1996 | Jommi et al. |
| 5,621,111 A | 4/1997 | Lui et al. |
| 5,663,361 A | 9/1997 | Towson et al. |
| 5,789,599 A | 8/1998 | Davis et al. |
| 5,908,937 A | 6/1999 | Jommi et al. |
| 5,958,888 A | 9/1999 | Macy et al. |
| 6,054,434 A | 4/2000 | Kropp et al. |
| 6,239,112 B1 | 5/2001 | Macy et al. |
| 6,270,768 B1 | 8/2001 | O'Connell et al. |
| 6,271,255 B1 | 8/2001 | Leadlay et al. |
| 6,339,063 B1 | 1/2002 | Kropp et al. |
| 6,437,151 B2 | 8/2002 | Leadlay et al. |
| 6,472,371 B1 | 10/2002 | Dirlam et al. |
| 6,514,945 B1 | 2/2003 | Boettner |
| 6,790,867 B2 | 9/2004 | Kohan et al. |
| 2004/0082553 A1 | 4/2004 | Boojamra et al. |
| 2005/0014828 A1 | 1/2005 | Murthy et al. |
| 2005/0182031 A1 | 8/2005 | Hecker et al. |
| 2005/0182059 A1 | 8/2005 | Winzenberg et al. |
| 2005/0182138 A1 | 8/2005 | John et al. |
| 2005/0182139 A1 | 8/2005 | Shuster et al. |
| 2006/0063841 A1 | 3/2006 | Meyer et al. |
| 2006/0128779 A1 | 6/2006 | Winzenberg et al. |
| 2008/0188556 A1* | 8/2008 | Glinka et al. ............... 514/512 |

FOREIGN PATENT DOCUMENTS

| BE | 638 755 A | 4/1964 |
| BE | 669 982 A | 3/1966 |
| EP | 0 014 437 B1 | 8/1980 |
| FR | 4 604 M | 11/1966 |
| WO | WO 03/077828 A2 | 9/2003 |
| WO | WO 2005/009429 A1 | 2/2005 |

OTHER PUBLICATIONS

Banerjee, Anamitro et al., "Photoreleasable protecting groups based on electron transfer chemistry. Donor sensitized release of phenacyl groups from alcohols, phosphates and diacids," Tetrahedron, 55(44): 12699-12710 (1999).

Bolhofer, William, "The Preparation of Hydroxyphenylserines from benzyloxybenzaldehydes and Glycine," J. Am. Chem. Soc. 76:1322-26(1954).

(Continued)

*Primary Examiner* — James O Wilson
*Assistant Examiner* — Ebenezer O Sackey

(57) ABSTRACT

Novel fenicol compounds having useful properties as antibiotic prodrugs, are provided, together with methods of making and using these new compounds.

17 Claims, 6 Drawing Sheets

OTHER PUBLICATIONS

Bolton, Lance F. et al., "Detection of multidrug-resistant *Salmonella enterica* serotype typhimurium DT104 based on a gene which confers cross-resistance to florfenicol and chloramphenicol," J Clin Microbiol. May 1999;37(5):1348-51.

Von Dem Bruch, K. et al., "The 3-(3-pyridyl)allyloxycarbonyl (paloc) moiety—a stable, amino-protecting group for peptide syntheses in organic media and in water that is cleavable under neutral conditions," Angew. Chem. 29(12): 1457-1990.

Brunelle, Daniel, "Novel catalysis of o-nitrophenyl carbonates by p-dimethylaminonopyridine," Tetrahedron Lett. 23(17): 1739-1742 (1982).

Castro, Enrique A. et al., "Kinetic investigation of the phenolysis of phenyl 4-nitrophenyl and phenyl 2,4-dinitrophenyl carbonates," J. Chem. Soc. Perkin. Trans. 2(12):2351-2354 (2001).

Chen, C. et al., "Synthesis of (+)-CP-263,114" J. Am. Chem. Soc. 122 (30): 7424 -7425 (2000).

Chmielewski, Marcin K. et al., "Thermolytic Carbonates for Potential 5'-Hydroxyl Protection of Deoxyribonucleosides," J. Org. Chem., 68(26):10003-10012 (2003).

Cloeckaert, Axel et al., "Nonenzymatic chloramphenicol resistance mediated by IncC plasmid R55 is encoded by a floR gene variant," Antimicrobial Agents and Chemotherapy 45(8):2381-2 (2001).

Compendium of Veterinary Products, Seventh Edition, pp. 1841-1842, 2043 (2003).

Diaz, Monica et al., "CAL-B-Catalyzed Alkoxycarbonylation of A-Ring Stereoisomeric Synthons of $1\alpha$,25-Dihydroxyvitamin $D_3$ and $1\alpha$,25-Dihydroxy-19-*nor*-previtamin $D_3$: A Comparative Study. First Regioselective Chemoenzymatic Synthesis of 19-*nor*-A-Ring Carbonates," J. Org. Chem. 66(12):4227-4232 (2001).

Dubowchik, Gene M. et al., "Cathepsin B-sensitive dipeptide prodrugs. 2. Models of anticancer drugs paclitaxel (Taxol®), mitomycin C and doxorubicin," Bioorg. Med. Chem. Lett. 8(23):3347-3352 (1998).

Evans, David D. et al., "Analogues of Chloramphnicol. Part III," J. Chem. Soc. 1687-90 (1954).

Grehn, Leif et al., "A Simple Method for tert-Butoxycarbonylation of Amides," Acta Chemica Scandinavica B 40:745-750 (1986).

Greiner, Beate et al., "Nucleotides. Part LVII. Synthesis of phosphoramidite building blocks of 2-amino-2-deoxyribonucleosides: new compounds for oligonucleotide synthesis," Helv. Chim. Acta 81(8):1528-1544 (1998).

Hansch, Corwin, et al., "Structure-activity relationship of chloramphenicols," J Med Chem. Aug. 1973;16(8):917-22.

Harada et al., "Allyloxycarbonyl group as a protective group for the hydroxyl group in carbohydrates," Journal of Carbohydrate Chemistry 14(1):165-170 (1995).

Herbert, Richard B. et al., "Preparation of (2R,3S)-β-hydroxy-α-amino acids by use of a novel Streptomyces aldolase as a resolving agent for racemic material," Can. J. Chem. 72:114-17 (1994).

Hoflack, G. et al., "Efficacy of tilmicosin phosphate (Pulmotil premix) in feed for the treatment of a clinical outbreak of *Actinobacillus pleuropneumoniae* infection in growing finishing pigs," J Vet Med B Infect Dis Vet Public Health 48(9):655-64 (2001).

Ishizuka, Tadao et al., "Mild and Selective Ring-Cleavage of Cyclic Carbamates to Amino Alcohols," Tetrahedron Letters 28:4185-88 (1987).

Jommi, Giancarlo et al., "2-Oxazolidinones as Regioselective Protection of β-Amino Alcohols in the Synthesis of 2-Amino-1-Aryl-3-Fluoro-1-Proponals," Gazzetta Chimica Italiana 116:485-89 (1986).

Jommi, Giancarlo et al., "Mild Recovery of β-amino Alcohols from the Corresponding 2-Oxazolidinones," Gazzetta Chimica Italiana 118:75-76 (1988).

Kenar, James A. et al., "Synthesis and characterization of dialkyl carbonates prepared from mid-, long-chain, and guerbet alcohols," J. Am. Oil Chem. Soc. 81(3):285-291 (2004).

Keyes, Kathleen et al., "Detection of florfenicol resistance genes in *Escherichia coli* isolated from sick chickens," Antimicrob Agents Chemother. 44(2):421-4 (2000).

Kim, Eun-Heui et al., "Sequence Analysis of the Florfenicol Resistance Gene Encoded in the Transferable R-Plasmid of a Fish Pathogen, *Pasteurella piscicida*,". Microbiol. Immunol. 40:665-69 (1996).

Kozikowski, Alan P. et al., "Novel PI Analogues Selectively Block Activation of the Pro-survival Serine/Threonine Kinase Akt," J. Am. Chem. Soc., 125 (5):1144-1145 (2003).

Kryczka, B., "Syntheses de carbonates et carbamates benzyliques et allvliques," Bull. Soc. Chim. Belg. 101(2) :147-158 (1992).

Lal, Gauri S. et al., "Bis(2-methoxyethyl)aminosulfur Trifluoride: A New Broad-Spectrum Deoxofluorinating Agent with Enhanced Thermal Stability," J. Org. Chem. 64:7048-54(1999).

Lam, Patrick Y.S. et al., "New Aryl/Heteroaryl C-N Bond Cross-coupling Reactions via Arylboronic Acid/Cupric Acetate Arylation," Tetrahedron Letters 39:2941-44 (1998).

Lam, Patrick Y.S. et al., "Copper Promoted Aryl/Saturated Heterocyclic C-N Bond Cross-Coupling with Arylboronic Acid and Arylstannane," Synlett 5 :674-76 (2000).

Lam, Patrick Y.S. et al., "Copper-catalyzed general C-N and C-O bond cross-coupling with arylboronic acid," Tetrahedron Letters 42:3415-18 (2001).

Li, Hong-Yu et al., "Synthesis of DNA Oligomers Possessing a Covalently Cross-Linked Watson-Crick Base Pair Model," Angewandte Chemie International Edition 40(8):1471-1475 (2001).

Imori, Takamasa et al., "A novel intramolecular decarboxylative glycosylation via mixed carbonate," Tetrahedron Lett. 37(13):2267-2270 (1996).

Mindl et al., "Alkoxycarbonylation of alcohols and phenols by nitrosoformates," Collect. Czech. Chem. Commun. 61(7)1053-1063 (1996).

Mitscher, Lester A. et al., "Circular dichroism studies of aryl diasteroisomers. 3. Cupra A spectra of chloramphenicol derivatives," J Med Chem.16(2):98-101 (1973).

Moris, Franciso et al., "Enzymatic acylation and alkoxycarbonylation of α-, xylo-, anhydro-, and arabino-nucleosides," Tetrahedron 49(44):10089-10098 (1993).

Moris, Franciso et al., "A novel and convenient route to 3'-carbonates from unprotected 2'-deoxynucleosides through an enzymic reaction," J. Org. Chem. 57(8): 2490-2492 (1992).

Morris et al., "Analogues of Chloramphenicol. Part I," J. Chem. Soc. 1680-86 (1954).

National Office of Animal Health, Antibiotics for Animal—An Overview, Briefing Document No. 6.

Nielsen, Peter E., et al., "Light Sensitive Chloramphenicol Analogues," Acta Chemica Scandinavica B 29:662-66 (1975).

Olofson, R.A. et al., "A regiospecific and stereospecific route to enol carbonates and carbamates: closer look at a "naked anion"," Tetrahedron Lett. 21:819-822 (1980).

PCT International Search Report dated Jun. 27, 2005 for corresponding PCT Application No. PCT/US2004/043199.

Peri, Francesca et al., "Preparation of Bicyclo[3.2.0]heptane-2-endo,7-endo-diols: 1,3-Diols with a Chiral Rigid Backbone," J. Org. Chem., 69 (4):1353-1356 (2004).

Pines, Seemon et al., "Substituent Effects in the Reaction of N-Benzoyl-β-arylserinates with Thionyl Chloride," J. Org. Chem. 37:292-97(1972).

Pulido, Rosalino et al., "Enzymatic regioselective alkoxycarbonylation of hexoses and pentoses with carbonate oxime esters," J. Chem. Soc. Perkin Trans. 1(5):589-592 (1993).

Rebstock, M.C. et al., "Chloramphenicol (Chloromycetin). IV. Chemical Studies," J. Am. Chem. Soc. 71:2458-62 (1949).

Rege, K. et al., "Chemoenzymatic synthesis and high-throughput screening of an aminoglycoside-polyamine library: identification of high-affinity displacers and DNA-binding ligands," J Am Chem Soc. 126(39):12306-15 (2004).

Schirmesiter, Helga et al., "Nucleosides. Part II The 2-(4-nitrophenyl) ethoxycarbonyl (npeoc) and 2-(2-,4-dinitrophenyl)ethoxycarbonyl (dnpeoc) groups for protection of hydroxy functions in ribonucleosides and 2 -deoxyribonucleosides," Helv. Chim. Acta 76(1):385-401 (1993).

Shaw, W.V. et al., "Chloramphenicol Resistance by Enzymatic Acetylation: Comparative Aspects," Antimicrobial Agents and Chemotherapy 257-63(1968).

Shue, Youe-Kong et al., "Novel methodology for the synthesis of trans-alkene dipeptide isosteres," J. Org. Chem. 56(6):2107-2111 (1991).

Supniewski et al., "Synthesis and Biological Properties of 1-Methytseleno-p-diphenyl-2-dichloroacetamino-1,3-propanediol" Bulletin de l'Academie Polonaise des Sciences, Serie des Sciences Biologiques 9, 231-234 (1961).

Supniewski et al., "Synthesis and Biological Properties of 1-Methylthio-p-diphenyl-2-dichloroacetamino-1,3-propanediol" Bulletin de l'Academie Polonaise des Sciences, Serie des Sciences Biologiques 9, 235-239 (1961).

Takamizawa, A. et al., "Studies of the Pyrimidine Derivatives. XXV.* The Reaction of Alkoxycarbonylthiocyanates and Related Compounds with the Sodium Salt of Thiamine," Bull. Chem. Soc. Jpn. 36(9):1214-1220 (1963).

Von Strandtmann, Maximilian et al.,"Synthesis of p-acyl analogs of chloramphenicol and their antimicrobial properties," J Med Chem. Sep. 1967;10(5):888-90.

Wang, Haiyan et al., "Solid phase synthesis of neutral oligonucleotide analogues," Tetrahedron Lett. 32(50): 7385-7388 (1991).

Weber N. et al., "Steryl and stanyl esters of fatty acids by solvent-free esterification and transesterification in vacuo using lipases from *Rhizomucor miehei, Candida antarctica*, and *Carica papaya*," J Agric Food Chem. 49(11):5210-6 (2001).

Whalen, Lisa J. et al., "Resolution of a chiral alcohol through lipase-catalyzed transesterification of its mixed carbonate by poly(ethylene glycol) in organic media," Tetrahedron: asymmetry 11(6):1279-1288 (2000).

Wuts, Peter G. et al., "New Process for the Preparation of Methyl Carbonates," Org. Lett. 5(9):1483-1485 (2003).

Yu, Kuo-Long et al., "Retinoic Acid Receptor $\beta$, $\gamma$-Selective Ligands: Synthesis and Biological Activity of 6-Substituted 2-Naphthoic Acid Retinoids," J. Med. Chem. 39:2411-21(1996).

Snyder et al., "Common bacteria whose susceptibility to antimicrobials is no longer predictable," Leb. Med. J. 48(4):206-214 (2000).

* cited by examiner (Scheme 1)

(Scheme 2)

(Scheme 3)

(Scheme 4)

(Scheme 5)

(Scheme 6)

(Scheme 7a)

(Scheme 7b)

CARBONATES OF FENICOL ANTIBIOTICS

CROSS-REFERENCE TO RELATED APPLICATIONS

This application is a non-provisional application that claims priority under 35 U.S.C. §119(e) of provisional applications U.S. Ser. No. 60/754,967 filed Dec. 29, 2005, and U.S. Ser. No. 60/781,487 filed Mar. 10, 2006, the contents of both of which are hereby incorporated by reference in their entireties.

FIELD OF THE INVENTION

The present invention relates to carbonate prodrugs of fenicol compounds having improved solubility and reduced viscosity in suitable solvent carriers.

BACKGROUND OF THE INVENTION

Chloramphenical, thiamphenicol and florfenicol are broad spectrum antibiotics known generically as "fenicols." Florfenicol is a broad spectrum antibiotic with activity against many gram-negative and gram-positive bacteria. Florfenicol is useful for the prevention and treatment of bacterial infections due to susceptible pathogens in mammals, birds, reptiles, fish and shellfish. One of its primary uses is in the treatment of pneumonia and associated respiratory infections in cattle (often referred to generically as Bovine Respiratory Disease or BRD) caused by *Mannhemia haemolytica, Pasteurella multocida* and(or) *Histophilus somni*. It is also indicated in the treatment of infectious pododermatitis in cattle caused by *Fusobacterium necrophorum* and/or *Prevotella melaninogenicus*, swine respiratory disease caused by *Pasteurella multocida, Actinobacillus pleuropneumoniae, Streptococcus suis, Salmonella cholerasuis* and(or) *Mycoplasma* spp., colibacillosis in chickens caused by *Escherichia coli*, enteric septicemia in catfish caused by *Edwardsiella ictaluri*, and furunculosis in salmon caused by *Aeromonas salmonicida*. Other genera of bacteria that have exhibited susceptibility to florfenicol include *Enterobacter, Klebsiella, Staphylococcus, Enterococcus, Bordetella, Proteus*, and *Shigella*. In particular, chloramphenicol resistant strains of organisms such as *K. pneumoniae, E. cloacae, S. typhus* and *E. coli* are susceptible to florfenicol.

As shown below, florfenicol is a structural analog of thiamphenicol which, in turn, is a derivative of chloramphenicol, wherein the aromatic nitro group that has been implicated in chloramphenicol-induced, non-dose related irreversible aplastic anemia in humans is replaced with a methylsulfonyl group.

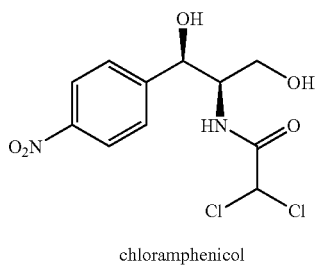

chloramphenicol

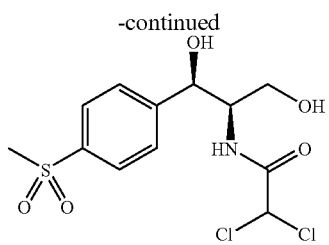

thiamphenicol

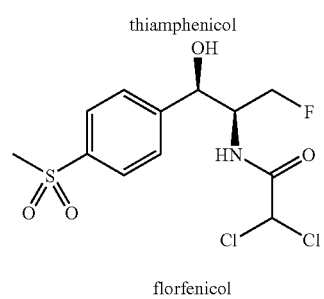

florfenicol

Florfenicol has a fluorine atom in place of the primary hydroxyl group of chloramphenicol and thiamphenicol. This renders florfenicol less susceptible to deactivation by bacteria containing the plasmid-encoded enzyme, chloramphenicol acetyl transferase (CAT), which acetylates the primary hydroxyl group of chloramphenicol and thiamphenicol. The acetylation prevents these antibiotics from binding to ribosomal subunits of susceptible bacteria. The binding of this class of antibiotic to ribosomal subunits is the primary (but not the sole) mechanism of action of chloramphenicol and thiamphenicol in inhibiting peptidyl transferase, which is responsible for the transfer of amino acids to growing peptide chains and subsequent protein formation, in bacteria.

Florfenicol is most often administered to a subject which can benefit from its advantages either orally, subcutaneously, or parenterally, the latter being primarily intramuscular or intravenous. Given the need for economical, single-dose treatment in the veterinary setting, there remains a need for new formulations of florfenicol at high concentrations.

In addition, there is also a need for a form of florfenicol that is capable of maintaining effective plasma antibiotic levels for prolonged periods of time, in order to achieve improved economies in administration, e.g., to more readily provide single dose treatment, particularly in a veterinary setting.

In an effort to extend the benefits of a single injection of florfenicol, the art has considered florfenicol ester derivatives as prodrugs. For example, Murthy et al., in published U.S. patent application No. 2005/0014828, have described esterified florfenicols such as florfenicol acetate, florfenicol propionate, florfenicol butyrate, florfenicol pentanoate, florfenicol hexanoate, florfenicol heptanoate, florfenicol octanoate, florfenicol nanoate, florfenicol decanoate, florfenicol undecanoate, florfenicol dodecanoate, and florfenicol phthalate, and the like.

Florfenicols with enhanced water solubility, and prodrug activity in the form of florfenicol phosphate esters are also described in co-owned published U.S. patent application No. 2005/0182031.

Nevertheless, there remains a longstanding need in the art for additional fenicols, with enhanced solubility in suitable carriers that can provide economical single dose treatment.

The citation of any reference herein should not be construed as an admission that such reference is available as "prior art" to the instant application.

SUMMARY OF THE INVENTION

Accordingly, in order to address the above-described needs, the invention provides for carbonate derivatives of fenicols having useful prodrug properties. In one embodiment of the invention there are provided fenicol carbonate compounds corresponding to Formula (I):

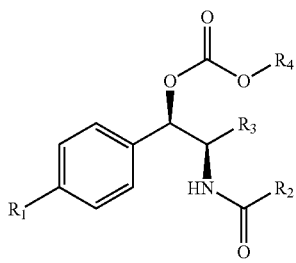

Formula I wherein $R_1$ is selected from the group consisting of:

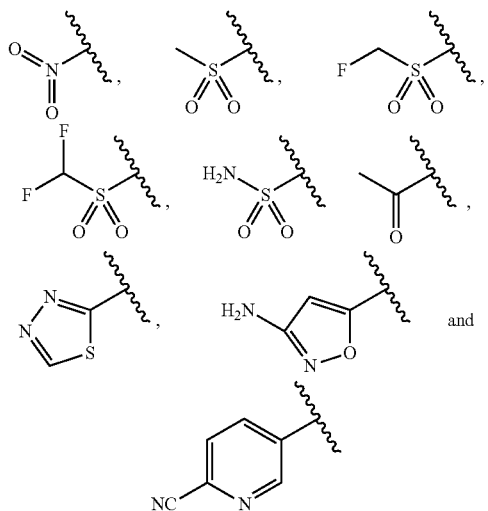

$R_2$ is selected from the group consisting of dichloromethyl, difluoromethyl, chlorfluoromethyl, chloromethyl and methyl, $R_3$ is selected from the group consisting of hydroxymethyl, fluoromethyl, difluoromethyl, trifluoromethyl and $CH_2O\text{—}C(O)O\text{—}R_5$, $R_4$ and $R_5$ are independently selected from the group consisting of substituted or unsubstituted $C_{1-10}$ straight, branched or cyclo alkyl, substituted or unsubstituted $C_{1-10}$ alkoxyalkyl, $C_{1-10}$ aryl, $C_{1-10}$ arylalkyl, substituted or unsubstituted $C_{1-10}$ straight, branched or cycloalkenyl. Preferably, $R_3$ is $CH_2F$. In a particular embodiment, $R_1$ is $CH_3SO_2$, $R_2$ is $CHCl_2$ and $R_3$ is $CH_2F$. Further, when $R_1$ is $NO_2$, $R_3$ is not $CH_2O\text{—}C(O)O\text{—}R_5$.

In another embodiment, $R_4$ and $R_5$ are independently substituted with a moiety selected from the group consisting of methyl, methoxy, carboxy, carboalkoxy and acyloxy.

In yet another embodiment, $R_4$ and $R_5$ are independently selected from the group consisting of methyl, ethyl, propyl, isopropyl, n-butyl, tert-butyl, isobutyl, pentyl, isopentyl, n-hexyl, n-heptyl, n-octyl, n-nonyl, n-decyl, n-dodecyl, n-octadecyl, 2-methyl-butyl, 1-ethyl-propyl, 3-methyl-prop-2-enyl, 2-methoxy-ethyl, 2-ethoxy-ethyl, 2-propoxy-ethyl, 2-butoxy-ethyl, 1-methyl-2-methoxy-ethyl, cyclopropyl-methyl, cyclopentyl-methyl, cyclohexyl-methyl, cyclopropyl, cyclobutyl, cyclopentyl, cyclohexyl, 3,7-dimethyloct-6-enyl, benzyl, 2-methyl-benzyl, 3-methyl-benzyl, 4-metyl-benzyl, 2-methoxy-benzyl, 3-methoxy-benzyl, 4-methoxy-benzyl, methyl-2-furyl, 2-(methoxy-ethoxy)-ethyl, 2-(ethoxy-ethoxy)-ethyl, 2-[2-(methoxy-ethoxy)-ethoxy]-ethyl, 2-[2-(ethoxy-ethoxy)-ethoxy]-ethyl, 2-(hydroxy-ethoxy)-ethyl, 2-[2-(hydroxy-ethoxy)-ethoxy]-ethyl, 2-acetoxy-ethyl, 2-(acetoxy-ethoxy)-ethyl, 3-acetoxy-propyl, 2-carboxy-ethyl, 3-carboxy-propyl, 4-carboxy-butyl, 2-methoxycarbonyl-ethyl, 3-methoxycarbonyl-propyl, 4-methoxycarbonyl-butyl, 2-methoxycarbonyl-benzyl, 3-methoxycarbonyl-benzyl, 4-methoxycarbonyl-benzyl, 1-ethoxycarbonyl-ethyl, 1-methoxycarbonyl-ethyl, phenyl, 4-metyl-phenyl, 4-methoxy-phenyl, 4-carboxy-phenyl, 2-carboxy-phenyl, 4-methoxycarbonyl-phenyl, 2-methoxycarbonyl-phenyl and 4-acetylamino-phenyl.

In a further embodiment, $R_1$ is selected from the group consisting of

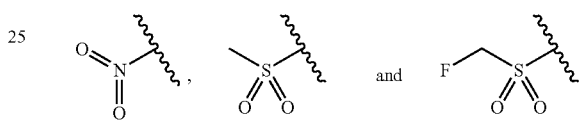

$R_2$ is dichloromethyl or difluoromethyl, and $R_3$ is selected from the group consisting of hydroxymethyl, fluoromethyl and $CH_2O\text{—}C(O)O\text{—}R_5$, and optionally, $R_4$ is selected from the group consisting of methyl, ethyl, propyl, isopropyl, n-butyl, tert-butyl, isobutyl, pentyl, isopentyl, n-hexyl, n-heptyl, n-octyl, n-nonyl, n-decyl, n-dodecyl, n-octadecyl, 2-methyl-butyl, 1-ethyl-propyl, 3-methyl-propen-2-enyl, 2-methoxy-ethyl, 2-ethoxy-ethyl, 2-propoxy-ethyl, 2-butoxy-ethyl, 1-methyl-2-methoxy-ethyl, cyclopropyl-methyl, cyclopentyl-methyl, cyclohexyl-methyl, cyclopropyl, cyclobutyl, cyclopentyl, cyclohexyl, 3,7-dimethyloct-6-enyl, benzyl, 2-methyl-benzyl, 3-methyl-benzyl, 4-metyl-benzyl, 2-methoxy-benzyl, 3-methoxy-benzyl, 4-methoxy-benzyl, methyl-2-furyl, 2-(methoxy-ethoxy)-ethyl, 2-(ethoxy-ethoxy)-ethyl, 2-[2-(methoxy-ethoxy)-ethoxy]-ethyl, 2-[2-(ethoxy-ethoxy)-ethoxy]-ethyl, 2-(hydroxy-ethoxy)-ethyl, 2-[2-(hydroxy-ethoxy)-ethoxy]-ethyl, 2-acetoxy-ethyl, 2-(acetoxy-ethoxy)-ethyl, 3-acetoxy-propyl, 2-carboxy-ethyl, 3-carboxy-propyl, 4-carboxy-butyl, 2-methoxycarbonyl-ethyl, 3-methoxycarbonyl-propyl, 4-methoxycarbonyl-butyl, 2-methoxycarbonyl-benzyl, 3-methoxycarbonyl-benzyl, 4-methoxycarbonyl-benzyl, 1-ethoxycarbonyl-ethyl, 1-methoxycarbonyl-ethyl, phenyl, 4-metyl-phenyl, 4-methoxy-phenyl, 4-carboxy-phenyl, 2-carboxy-phenyl, 4-methoxycarbonyl-phenyl, 2-methoxycarbonyl-phenyl and 4-acetylamino-phenyl.

In a still further embodiment, $R_1$ is $CH_3SO_2$ or $NO_2$, $R_2$ is $CHCl_2$, $R_3$ is OH and $R_4$ is ethyl, or alternatively, $R_1$ is $CH_3SO_2$ or $NO_2$, $R_2$ is $CHCl_2$, $R_3$ is

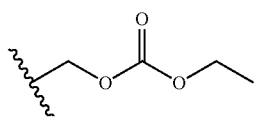

and $R_4$ is ethyl.

Preferably, the inventive fenicol carbonate is selected from the following group of compounds:

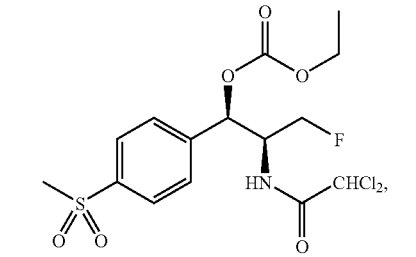

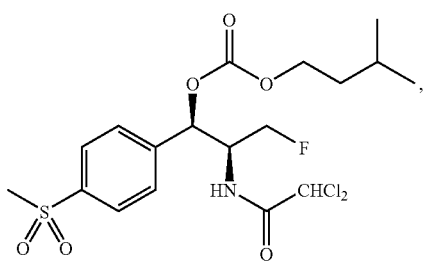

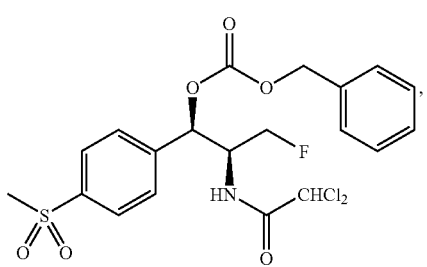

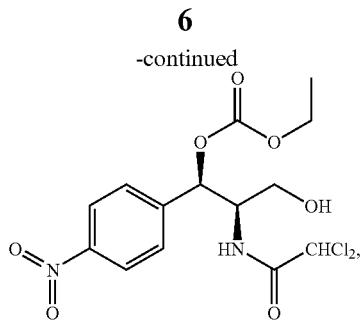

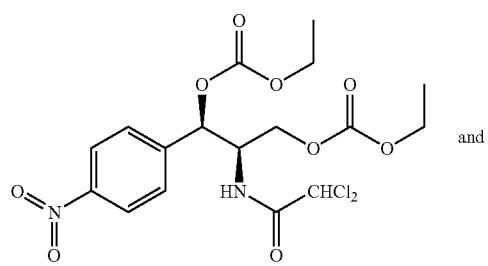

and

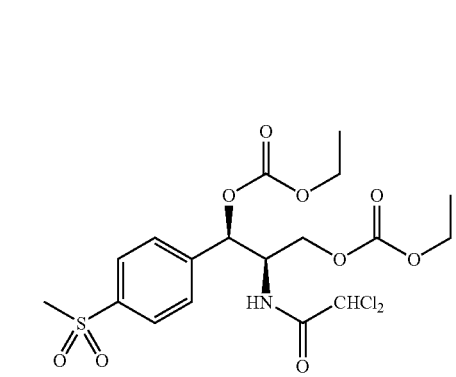

The invention also specifically includes the compounds exemplified herein, including the fenicol carbonates listed by Table 2, herein below.

Further, it is also contemplated that the inventive compounds include bis-fenicol carbonates. For example, such bis-fenicol carbonates include compounds comprising the structure of Formula II, below.

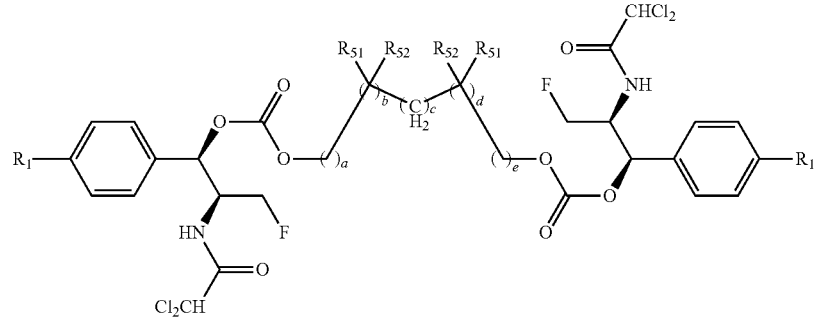

Formula II wherein $R_1$ is selected from the group consisting of

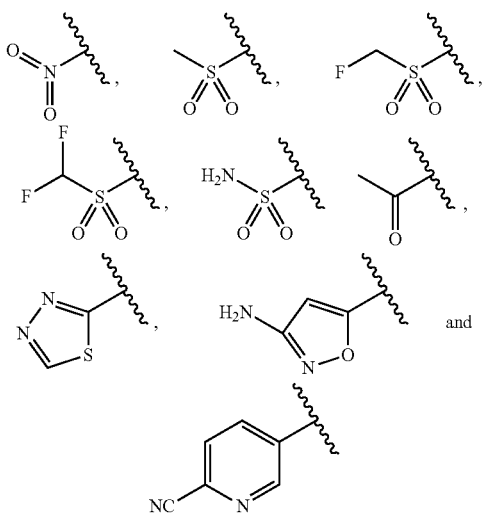

and wherein a, c and e are integers that independently range in value from 0 through 4, b and d are integers that independently range in value from 0 through 2, provided that the sum of integers a, b, c, d and e ranges in value from 2 to 8, and $R_{51}$ and $R_{52}$ are independently selected from the group consisting of H, methyl, hydroxyl, methoxy, and acetoxy. Preferably, the sum of a, b, c, d and e ranges in value from 2 through 4.

More preferably, the invention comprises the compound of Formula II wherein $R_1$ is

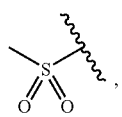

and $R_3$ is $CH_2F$.

Even more preferably, the invention comprises the compound of Formula II having a structure selected from the group consisting of:

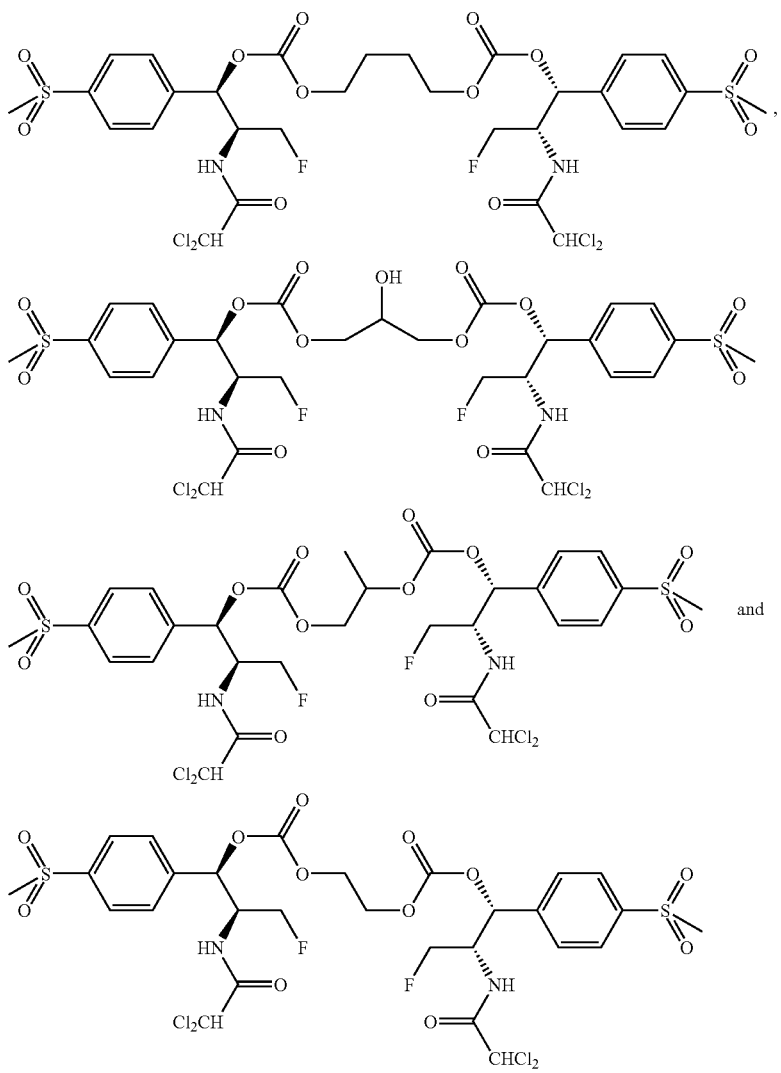

In a further embodiment, the invention also includes a pharmaceutical composition comprising an effective amount of a fenicol carbonate compound according to Formula I or Formula II, or a solvate thereof, together with a pharmaceutically acceptable excipient or solvent. Preferably, the fenicol carbonate comprises from about 80 percent to about 5 percent by weight of the composition.

Preferably, the pharmaceutically acceptable solvent comprises at least one pharmaceutically acceptable alcohol, e.g., such as benzyl alcohol. Generally, the alcohol content of the pharmaceutical composition ranges from about 5% to about 98%, by weight, of the composition. Preferably, the alcohol content ranges from about 10% to about 90%, by weight, of the composition. More preferably, the alcohol content ranges from about 20% to about 45%, by weight, of the composition. A benzyl alcohol concentration of up to 45% by weight is particularly advantageous.

The invention further includes a pharmaceutical composition comprising an effective amount of the fenicol carbonate of Formula I, wherein $R_1$ is $CH_3SO_2$, $R_2$ is $CHCl_2$ and $R_3$ is $CH_2F$, together with pharmaceutically acceptable excipients or solvents.

The invention still further includes a pharmaceutical composition comprising an effective amount of a fenicol carbonate of Formula I or Formula II, together with pharmaceutically acceptable excipients or solvents and comprising a corresponding fenicol, wherein the corresponding fenicol is a fenicol that is identical to the fenicol released in vivo by the fenicol carbonate of Formula I or Formula II, respectively.

It is also contemplated that the inventive pharmaceutical compositions further comprise at least one additional therapeutic agent that can be administered to the animal in need thereof before, after, and/or simultaneously with the inventive fenicol carbonate.

The additional pharmaceutical agent is, for example, a florfenicol and/or any other type of agent suitable for administration to an animal in need thereof. Such additional agent includes, for example, an endectocidal compound, such as an avermectin. The avermectin is, simply by way of example, selected from the group of Ivermectin, Doramectin, Abamectin, Selamectin, Emamectin, Eprinomectin, Moxidectin, Milbemycin, and combinations thereof. Preferably, the avermectin compound is present in an amount ranging from about 0.03% w/v to about 20% w/v. The additional agent can also further comprise a flukicide, optionally combined with an endoctocidic agent, or other agent as described in greater detail hereinbelow.

In yet a still further embodiment, the invention includes a pharmaceutical composition comprising the fenicol carbonate of Formula I, in combination with a fenicol compound of Formula III.

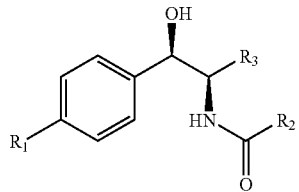

Formula III wherein the fenicol carbonate of Formula I and the fenicol of Formula III are present in a ratio ranging from 50:1 to 1:50, by weight, and wherein $R_1$ is $CH_3SO_2$, $R_2$ is $CHCl_2$ and $R_3$ is OH or F. $R_1$, $R_2$ and $R_3$ of Formula III are defined as for Formula I, supra. An analogous composition, comprising Formula II and Formula III, is also contemplated, employing the same or analogous ratios. The pharmaceutical compositions of the present invention can be administered to animals or fish in prophylactically-effective amounts, and/or for metaphylaxis, as a need and/or the practice merits.

Corresponding methods of administering prophylactically-effective amounts of the pharmaceutical compositions of the present invention and/or for metaphylaxis, as a need and/or the practice merits, are also provided by the present invention. The present invention also provides methods of treating or preventing a disease or disorder in an animal in need thereof. Such methods can comprise administering a pharmaceutically effective amount of the fenicol carbonate of Formula I and/or Formula II, including any of the compounds of Examples 1-30, as described hereinbelow. An effective amount ranges, for example, from about 1 to about 150 mg/kg of the animal to be treated. Broadly, the animal to be treated is any animal that will benefit from administration of the invention compounds. Generally, the animal to be treated is a mammal, *avian,* fish, reptile or invertebrate and includes any of the animals listed in greater detail hereinbelow.

The invention further provides processes for synthesizing the compound of Formula I, comprising reacting a fenicol compound with a corresponding chloroformate in a suitable solvent. The suitable solvent can include, for example, chlorinated solvents, ester solvents, polyether solvents, formaldehyde acetal ethers, cyclic ethers, ketones, mixed ether-ester solvents, and diethylene glycols, and preferably includes tetrahydrofuran.

The synthetic process is preferably conducted in the presence of a catalyst, e.g., 4-dimethylamino-pyridine, 4-methyl pyridine, pyridine and combinations thereof.

The synthetic process is preferably conducted in the presence of an acid scavenger, e.g., triethylamine, pyridine, sodium carbonate, sodium bicarbonate, potassium carbonate and combinations thereof.

The synthetic process is preferably conducted, wherein the chloroformate is

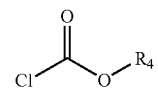

wherein $R_4$ is as defined as for Formula I, supra.

The synthetic process is preferably conducted, wherein the fenicol compound has the structure of:

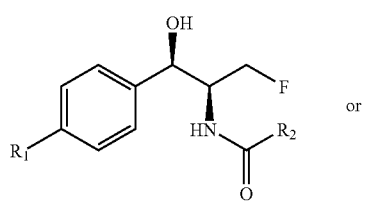

or

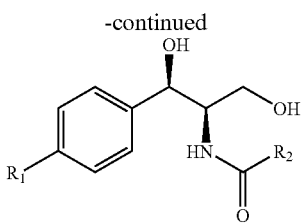

and the chloroformate is present in a molar excess, relative to the fenicol compound, during the reaction. $R_1$ and $R_2$ are as defined supra for Formula I.

The process for synthesizing the compound of Formula II, comprises reacting a fenicol compound with a corresponding bis-chloroformate in a suitable solvent, wherein the fenicol compound is present in a molar excess, relative to the chloroformate.

Preferably, in the process for preparing the compound of Formula II, the fenicol is a compound as follows,

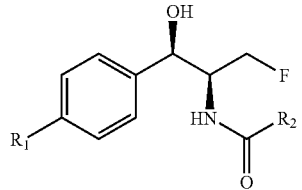

and the bis-chloroformate is preferably

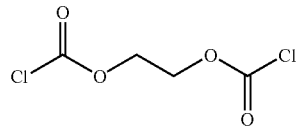

$R_1$ and $R_2$ are as defined supra for Formula I and or Formula II.

DETAILED DESCRIPTION OF THE INVENTION

Figure 1A:
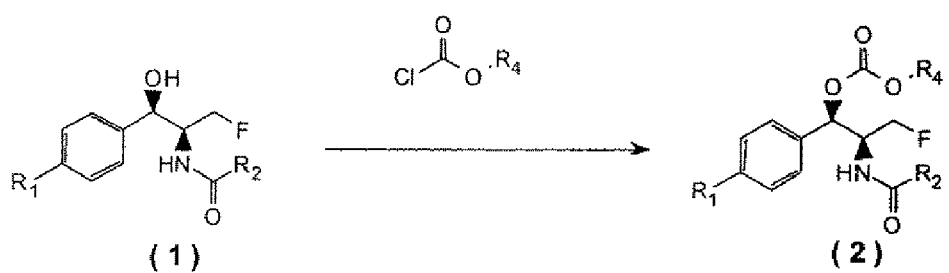
FIG. 1A illustrates reaction Scheme 1 for the synthesis of florfenicol and florfenicol analog benzylic carbonate prodrugs using chloroformates.

Accordingly, the present invention provides a carbonate form of fenicol, e.g., a florfenicol prodrug. Such fenicol carbonates are, in general, sparingly soluble in water, but are very soluble in other suitable, nonirritating organic solvents useful for administration by injection, and that can be used to treat and/or prevent bacterial infections. The compounds according to the invention are readily converted to free, active antibiotic agent in vivo.

In order to more fully appreciate the instant invention, the following definitions are provided.

The use of singular terms for convenience in the description is in no way intended to be so limiting. Thus, for example, reference to "a microbe" includes reference to one or more of such microbes. The use of plural terms is also not intended to be limiting, unless otherwise specified. For example, phrases such as, "carbonate derivative of fenicol" refers to any carbonate derivative of fenicol identified herein, including a single such compound alone, or a combination of two or more such compounds, unless otherwise specified.

As used herein, the term, "approximately," is used interchangeably with the term "about" and generally signifies that a value is within twenty percent of the indicated value, unless otherwise indicated.

As used herein, the term "prodrug" denotes a compound that is a drug precursor which, upon administration to a subject, undergoes chemical conversion by metabolic or chemical processes to yield the active drug, e.g., a carbonate of a fenicol antibiotic is a prodrug that releases a fenicol antibiotic in vivo.

As used herein, the term benzylic denotes a substituent or a substitution attachment where a substituent or substituent attachment is at the aliphatic saturated carbon atom which is directly attached to a phenyl or substituted phenyl ring. The term benzylic carbonate denotes a carbonate substituent, O—(O)C—OR, attached to such benzylic position.

As used herein, a "pharmaceutical composition" refers to a formulation of the inventive compound, including solvates thereof, (e.g., a florfenicol prodrug) with a pharmaceutically acceptable excipient, and/or carrier. The inventive compound is present in the carrier in an amount of from about 1 to about 80 percent, by weight. In a particular embodiment, the carrier is a solvent of the inventive compound that is relatively nonirritating to living tissue, and that is suitable for injection, such as certain organic solvents.

Organic solvents vary considerably in their viscosity and as components of the formulation of fenicol and fenicol prodrugs they contribute to the viscosity of the final formulation. Therefore organic solvents of lower viscosity are preferred components of high concentration formulations of fenicols and fenicol prodrugs. For example, alcohols such as ethyl alcohol, isopropyl alcohol, benzyl alcohol, glycerol formal (e.g., an equilibrium mixture of 1,3-dioxan-5-ol and 1,3-dioxolan-4-yl methanol), low molecular weight mono-ethers of ethylene glycerol, represent examples of low viscosity solvents acceptable for injectable formulation. Other solvents of relatively low viscosity such as esters (benzyl acetate, ethylene glycol bis-acetate, propylene glycol bis-acetate), ethers (low molecular weight bis-ethers of ethylene glycol or propylene glycol) or amides (2-methylpyrolidinone, 2-pyrolidinone) can also be used as components of the solvent mixture lowering the overall viscosity of fenicol carbonate prodrug solutions. However, such solvents or combinations containing such solvents usually do not provide enough solubility for parent fenicol drugs. The desired high concentrations of fenicols in low viscosity solvents or solvent mixtures containing high proportions of low viscosity solvents can be still be achieved by the use of fenicol benzylic carbonate prodrugs. A preferred solvent is benzyl alcohol, in combination with optional excipients. More preferred is a carrier comprising triacetin/benzyl alcohol in the ratio of 2:1 (vol/vol).

An "excipient" refers to an inert substance added to a pharmacological composition to further facilitate administration of an active ingredient. Examples, of excipients without limitation, include, e.g., various sugars and types of starch, cellulose derivatives, gelatin, vegetable oils and polyethylene glycols, and art known stabilizers, colorants and the like, as needed.

The term "therapeutically-effective amount," as used herein, refers to that amount of a prodrug of the present invention that will hydrolyze sufficiently rapidly and in sufficient amounts to provide an active fenicol in a concentration at which it can relieve to some extent one or more of the symptoms of a bacterial infection in a subject. In particular embodiment, a therapeutically-effective amount refers to that amount of the inventive compound that, when administered to a subject, delivers an active antibiotic, e.g., a fenicol, to a subject in a sufficient plasma concentration to: (1) reduce, and preferably eliminate, the population of bacterial cells in a subject's body; (2) inhibit (i.e., slow, or preferably stop) proliferation of the bacterial cells; (3) inhibit (i.e., slow, preferably stop) spread of the bacterial infection; and/or (4) relieve (preferably eliminate) one or more symptoms associated with the infection.

The term "prophylactically-effective amount" refers to the amount of a prodrug of the present invention that when administered to an animal or fish results in a sufficient plasma concentration of the corresponding active antibiotic to significantly reduce the likelihood and/or extent of an infection due to bacteria that are susceptible to that active antibiotic. A prophylactically-effective amount of an inventive compound of the present invention may also be used subsequent to the administration of an earlier antibiotic regimen to maintain a reduced level (or elimination) of a population of bacterial cells in the animal or fish.

"Metaphylaxis" is the timely mass medication of an entire group of animals to eliminate or minimize an expected outbreak of disease, e.g. in one or more animals at high risk of infection. In one particular embodiment, high risk calves are light weight, commingled, long haul cattle with unknown health histories.

As used herein the term "Minimum Inhibitory Concentrations" is used interchangeably with "MIC". An "MIC50" is the concentration of the compound (e.g., the prodrug of the present invention) at which the growth of 50% of the isolates is inhibited. Similarly, MIC90 is the concentration of the compound at which the growth of 90% of the isolates is inhibited.

As used herein, in the context of the synthesis of the inventive compound, a "suitable" solvent refers to a solvent in which the reactants can dissolve and which does not adversely participate in the reaction, either by itself reacting with one or more components of the reaction mixture, or by interfering with the reaction of the components with one another. For any given reaction, selecting a suitable solvent is well within the ability of those skilled in the art and can be accomplished without undue experimentation.

Synthesis of Inventive Compounds

The following reaction schemes illustrate how the inventive compounds are prepared.

Scheme 1.

Synthesis of Florfenicol and Florfenicol Analog Benzylic Carbonate Prodrugs Using Chloroformates.

In one embodiment, applicable to fenicols having only a benzylic hydroxy group (e.g., florfenicol and its analogs) a convenient method of preparing benzylic carbonate prodrugs is illustrated by FIG. 1A. As shown, a fenicol compound (1) is reacted with a corresponding chloroformate to produce benzylic carbonate (2) in an appropriate solvent with or without a catalyst. $R_1$, $R_2$ and $R_4$ of all of the Figures are as defined as given above for the compound of Formula I. Suitable solvents include, for example, chlorinated solvents such as dichloromethane and 1,2-dichloroethane; ester solvents such as ethyl acetate, isopropyl acetate, isoamyl acetate, ethylene glycol diacetate, propylene glycol diacetate, glycerol triacetate; monoether solvents such as diethyl ether, diisopropyl ether, methyl tert-butyl ether; polyether solvents such as ethylene glycol ethers:dimethyl ethylene glycol ether, diethylene glycol ethers:diethyleneglycol dimethyl ether, diethylene glycol diethyl ether; formaldehyde acetal ethers such as dimethoxy methane, diethoxymethane, dibutoxymethane; cyclic ethers such as tetrahydrofuran, 1,3-dioxolane, 1,4-dioxane; ketone solvents such as acetone, methyl ethyl ketone, methyl isobutylketone; mixed ether/ester solvents as represented by monoethers of ethylene and diethylene glycol such as 2-methoxyethyl acetate, 2-ethoxyethyl acetate, 2-(methoxy-ethoxy)ethyl acetate, 2-(ethoxy-ethoxy)ethyl acetate. The examples provided below exemplify the use of tetrahydrofuran as the solvent.

The reaction converting fenicol to a benzylic prodrug optionally employs a molar (up to 3-fold) excess of chloroformate reagent over fenicol, a catalyst or combination of catalysts, combination of a catalyst and an acid scavenger, prolonged reaction times and elevated temperature. Preferred catalysts include, for example, 4-dimethylamino-pyridine, 4-methyl pyridine, and pyridine. Preferred acid scavengers include, for example, triethylamine, pyridine, sodium carbonate, sodium bicarbonate and potassium carbonate. The reaction is preferably conducted for a time period ranging from about 0.5 to about 10 hours, and at a temperature ranging from about 0° C. to about 50° C.

Typically the reaction is conducted by adding 1.5-2.0 equivalents of chloroformate in tetrahydrofuran solution to the tetrahydrofuran solution containing a fenicol, 1.0 equivalent of triethylamine and 0.5 equivalent of 4-N,N-dimethylaminopyridine at 0° C. and allowing the reaction to proceed to completion. Unreacted fenicol (if present after the reaction) may be completely removed by standard methods in the art, or optionally allowed to remain in the final purified benzyl carbonate prodrug material in order to provide initial increased levels of florfenicol immediately after administration.

The chloroformate reagent is prepared, for example, by reacting the corresponding alcohol with phosgene or phosgene equivalent (e.g., diphosgene, triphosgene). Advantageously, the resulting crude chloroformate solution can be used for the carbonate formation step without purification. Alternatively a commercial chloroformate can be used for the carbonate formation step if available. Commercial sources of suitable chloroformates include, e.g. Aldrich and Lancaster.

Scheme 2.

Synthesis of Benzylic/Primary Alcohol Bis Carbonate Prodrugs of Chloroamphenicol Type (Dihydroxyfenicols)

Figure 1B:
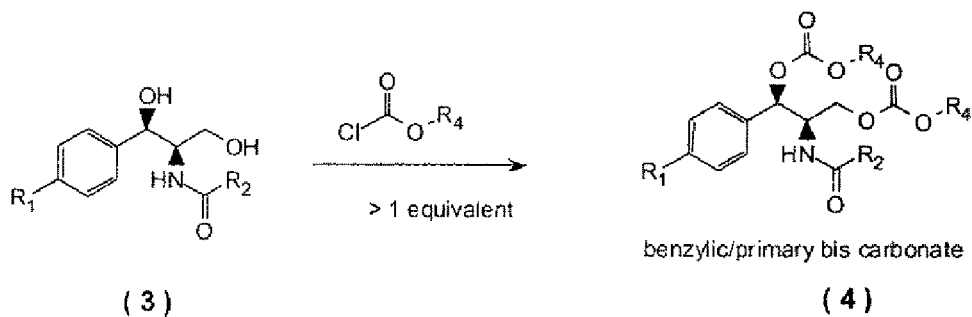
FIG. 1B illustrates reaction Scheme 2 for the synthesis of benzylic carbonate prodrug esters from dihydroxy fenicols (of the chloramphenicol type).

In a further embodiment, as illustrated by FIG. 1B. benzylic carbonate prodrug esters e.g., compound (4) can be also prepared from fenicols, e.g., compound (3), bearing two hydroxy groups (e.g., chloramphenicol, thiamfenicol, cetophenicol) by either selectively transforming the benzylic hydroxy group into corresponding carbonate prodrug or transforming both benzylic and the terminal primary hydroxy group into prodrug moieties to form a benzylic/primary alcohol bis carbonate prodrug.

Fenicols bearing two hydroxy groups (chloramphenicol type) can be converted into benzylic/primary alcohol bis-carbonate prodrugs by treating the corresponding fenicol with two or more equivalents of appropriate chloroformate using conditions similar to the ones described above for florfenicol-type fenicols. In such conditions the conversion of both hydroxy functionalities can be achieved simultaneously leading to benzylic/primary alcohol bis-carbonate prodrugs (Scheme 2).

Scheme 3.

Figure 2A:
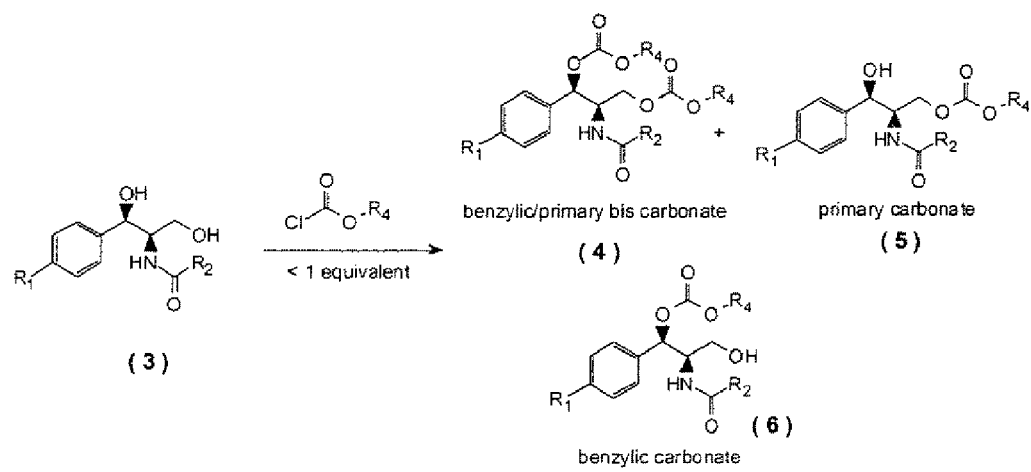
FIG. 2A illustrates reaction Scheme 3 (dihydroxy type fenicol, method A) for the synthesis of benzylic carbonate prodrug esters from dihydroxy fenicols using less than one molar equivalent of chloroformate reagent.

Synthesis of Benzylic Mono-Carbonate Prodrugs of Chloroamphenicol Type (Dihydroxyfenicols) Method A As illustrated by FIG. 2A, benzylic mono-carbonate prodrugs of chloroamphenicol-type (dihydroxy, $R_1=NO_2$) can be prepared using less than one molar equivalent of the chloroformate reagent and isolating the desired benzylic carbonate prodrug from the mixture of resulting mono and bis carbonates by crystallization, using the solvents shown by Table 5, or, e.g., by silica gel chromatography (Scheme 3).

Scheme 4

Figure 2B:
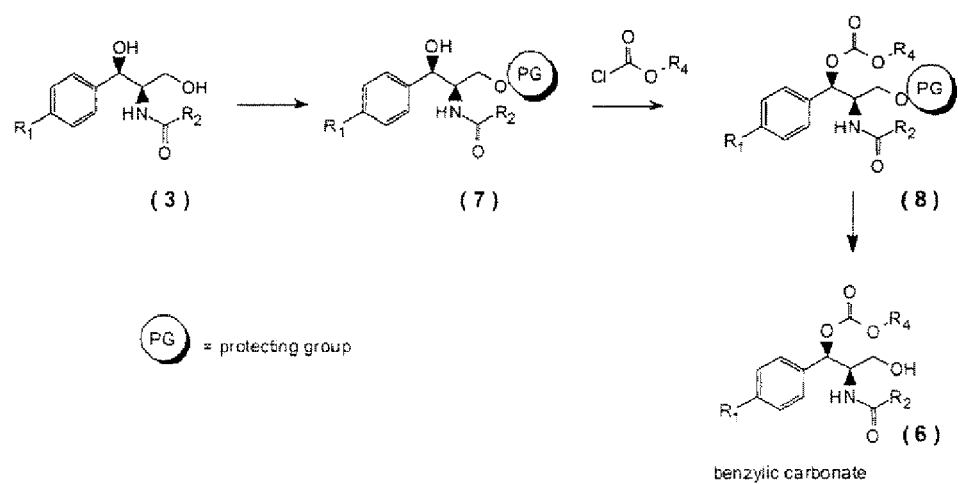
FIG. 2B illustrates reaction Scheme 4 (dihydroxy type fenicol, method B) for the synthesis of benzylic mono-carbonate prodrugs of dihydroxy fenicols (of the chloramphenicol type) using protecting group strategy.

Synthesis of Benzylic Mono-Carbonate Prodrugs of Chloroamphenicol Type (Dihydroxyfenicols)—Method B As illustrated by FIG. 2B, benzylic mono-carbonate prodrugs of chloroamphenicol-type (dihydroxy, $R_1=NO_2$) can be also prepared using the protecting group strategy by selectively introducing the protective group at the primary alcohol functionality which is followed by the reaction with the chloroformate selectively introducing the carbonate prodrug moiety at the benzylic alcohol (Scheme 4).

The protecting group used for protection of the primary alcohol may be an ester group such as formate, acetate, benzoate, pivaloate, a carbonate group such as tert-butoxycarbonate, a silyl protecting group such as trimethylsilyl, tert-butyldimethysilyl. Removal of the protecting group after the introduction of the desired carbonate prodrug moiety at the benzylic alcohol position of the fenicol molecule can be performed chemically using conditions appropriate for the removal of particular group (Protective Groups in Organic Synthesis; Theodora W. Greene, Peter G. M. Wuts; 3rd Edition, June 1999, John Wiley & Sons Inc) or by selective enzymatic hydrolysis allowing removal of the protecting group without affecting the benzylic carbonate prodrug moiety (Scheme 4).

Scheme 5.

Figure 3A:
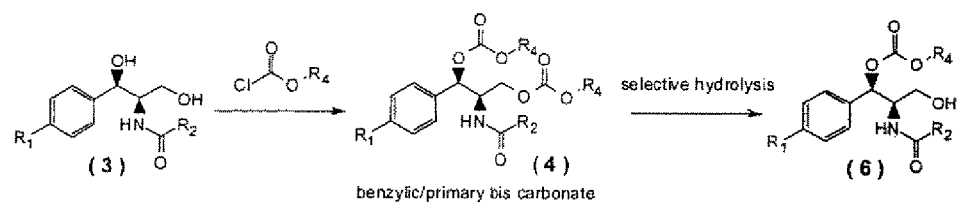
FIG. 3A illustrates reaction Scheme 5 (dihydroxy type fenicol, method C) for the synthesis of benzylic mono-carbonate prodrugs of dihydroxy fenicols (of the chloramphenicol type) using selective hydrolysis strategy.

Synthesis of Benzylic Mono-Carbonate Prodrugs of Chloroamphenicol Type (Dihydroxy)—Method C As illustrated by FIG. 3A, preparation of benzylic mono-carbonate prodrugs of chloroamphenicol type (dihydroxyfenicol, $R_1=NO_2$) can be also performed by initial preparation of benzylic/primary bis carbonate prodrugs followed by selective hydrolysis of the primary alcohol carbonate functionality performed chemically or enzymatically (Scheme 5).

Scheme 6.

Synthesis of Florfenicol and Florfenicol Analog Benzylic Carbonate Prodrugs Using X—(O)C—O—$R_4$ Reagents Other than Chloroformates.

Figure 3B:
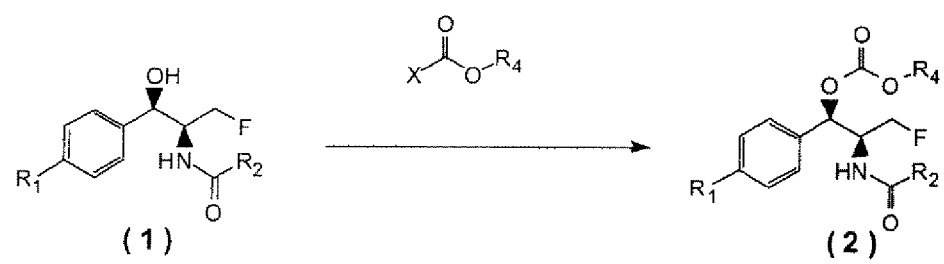
FIG. 3B illustrates reaction Scheme 6 for the synthesis of florfenicol and florfenicol analog benzylic carbonate prodrugs using X—(O)C—O—$R_4$ reagents other than chloroformates. The range of values for "X" is given by Table 1, below.

As illustrated by FIG. 3B, reagents other than chloroformates can be also used for preparation of benzylic carbonate prodrugs of fenicols. The reagents with leaving groups other than chloride can be used in order to introduce the carbonate moiety in a fashion analogous the reaction with chloroformate with or without the addition of a catalyst. Numerous examples of such reagents which can be used for such transformation exist in the literature and some are provided below.

With reference to FIG. 3B, Scheme 6, the value of X can include any one of the moieties tabulated by Table 1, as follows. Representative references are cited for each such moiety, each incorporated by reference herein.

TABLE 1

| Value of X | References |
| --- | --- |
| —F | Olofson R. A.; Cuomo, John; Tetrahedron Lett.; 21; 1980; 819-822; Nongkunsarn, Pakawan; Ramsden, Christopher A.; J. Chem. Soc. Perkin Trans. 1; 2; 1996; 121-122. |
| —CN | Adickes et al.; J. Prakt. Chem.; 2; 133; 1932; 313. Cen, Chuo; Layton, Mark E.; Sheehan, Scott M.; Shair, Matthew D.; J. Am. Chem. Soc.; 122; 30; 2000; 7424-7425. |
| —SCN | Takamizawa, A. et al.; Bull. Chem. Soc. Jpn.; 36; 9; 1963; 1214-1220. |
| —NCS | Takamizawa, A. et al.; Bull. Chem. Soc. Jpn.; 36; 9; 1963; 1214-1220. |
| —O-aryl or —O-aryl | Patent; Chininfabr. Zimmer & Co.; DE 117095.Weber, Nikolaus; Wetkamp, Petra; Mukherjee, Kumar D.; J. Agric. Food Chem.; 49; 11; 2001; 5210-5216. Kenar, James A.; Knothe, Gerhard; Copes, Ashley L.; J. Am. Oil Chem. Soc.; 81; 3; 2004; 285-291. |
| —NH—OH | Mindl, Jaromir; Halama, Ales; Cernosek, Zdenek; Collect. Czech. Chem. Commun.; 61; 7; 1996; 1053-1063. |
| imidazole | Kryczka, Boguslaw; Bull. Soc. Chim.Belg.; FR; 101; 2; 1992; 147-158. Iimori, Takamasa; Shibazaki, Takafumi; Ikegami, Shiro; Tetrahedron Lett.; 37; 13; 1996; 2267-2270 Whalen, Lisa J.; Morrow, Cary J.; Tetrahedron: Asymmetry; 11; 6; 2000; 1279-1288. Kozikowski, Alan P.; Sun, Haiying; Brognard, John; Dennis, Phillip A.; J. Am. Chem. Soc.; 125; 5; 2003; 1144-1145 Peri, Francesca; Binassi, Enrico; Manetto, Antonio; Marotta, Emanuela; Mazzanti, Andrea; Righi, Paolo; Scardovi, Noemi; Rosini, Goffredo; J. Org. Chem.; 69; 4; 2004; 1353-1356. Chmielewski, Marcin K.; Marchan, Vicente; Cieslak, Jacek; Grajkowski, Andrzej; Livengood, Victor; Muench, Ursula; Wilk, Andrzej; Beaucage, Serge L.; J. Org. Chem.; 26; 2003; 10003-10012. |
| imidazolium | Schirmeister, Helga; Himmelsbach, Frank; Pfleiderer, Wolfgang; Helv. Chim. Acta; 76; 1; 1993; 385-401. Greiner, Beate; Pfleiderer, Wolfgang; Helv. Chim. Acta; 81; 8; 1998; 1528-1544. Banerjee, Anamitro; Lee, Kwangjoo; Falvey, Daniel E.; Tetrahedron; 55; 44; 1999; 12699-12710. |
| —O—N-Succinimide | Shue, Youe-Kong; Carrera, George M.; Tufano, Michael D.; Nadzan, Alex M.; J. Org. Chem.; 56; 6; 1991; 2107-2111.; |

TABLE 1-continued

| Value of X | References |
|---|---|
| | Dubowchik, Gene M.; Mosure, Kathle Knipe, Jay O.; Firestone, Raymond A.; Bioorg. Med. Chem. Lett.; 8; 23; 1998; 3347-3352. |
| —O—N-Benzotriazole | Harada, Takeo; Yamada, Haruo; Tsukamoto, Hirokazu; Takahashi, Takashi; J. Carbohydr. Chem.; 14; 1; 1995; 165-170. |
| | Li, Hong-Yu; Qiu, Yao-Ling; Moyroud, Elisabeth; Kishi, Yoshito; Angew. Chem. Int. Ed.; 40; 8; 2001; 1471-1475; |
| | Angew. Chem.; 113; 2001; 1519-1523. |
| —N-Benzotriazole-N-oxide | Wuts, Peter G. M.; Ashford, Scott W.; Anderson, Andrew M.; Atkins, Joseph R.; Org. Lett.; 5; 9; 2003; 1483-1486. |
| —O—N=CR$_2$ | Pulido, Rosalino; Gotor, Vicente; J. Chem. Soc. Perkin Trans. 1; 5; 1993; 589-592. |
| | Moris, Franciso; Gotor, Vicente; J. Org. Chem.; 57; 8; 1992; 2490-2492. |
| | Moris, Francisco; Gotor, Vicente; Tetrahedron; 49; 44; 1993; 10089-10098. |
| | Diaz, Monica; Gotor-Fernandez, Vicente; Ferrero, Miguel; Fernandez, Susana; Gotor, Vicente; J. Org. Chem.; 66; 12; 2001; 4227-4232. |
| | Rege, Kaushal; Hu, Shanghui; Moore, James A.; Dordick, Jonathan S.; Cramer, Steven M.; J. Am. Chem.Soc.; 126; 39; 2004; 12306-12315. |
| Orto or para-nitrophenol | Brunelle, Daniel J.; Tetrahedron Lett.; 23; 17; 1982; 1739-1742. |
| | Bruch, Karsten von dem; Kunz, Horst; Angew. Chem.; 102; 12; 1990; 1520-1522. |
| | Wang, Haiyan; Weller, Dwight D.; Tetrahedron Lett.; 32; 50; 1991; 7385-7388. |
| | Iimori, Takamasa; Shibazaki, Takafumi; Ikegami, Shiro; Tetrahedron Lett.; 37; 13; 1996; 2267-2270. |
| 2,4-di-nitrophenol | Castro, Enrique A.; Angel, Mauricio; Pavez, Paulina; Santos, Jose G.; J. Chem. Soc. Perkin Trans. 2; 12; 2001; 2351-2354. |

Figure 7A:
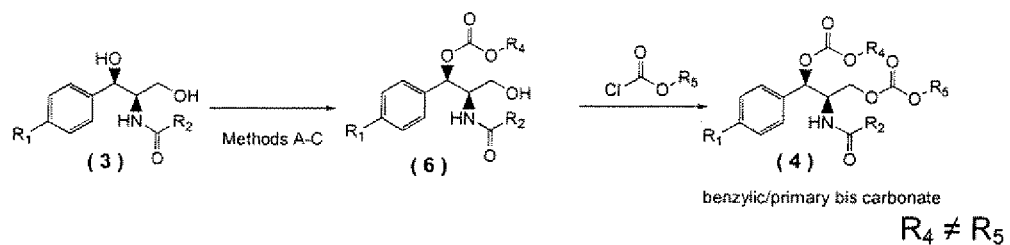
FIG. 7a illustrates reaction scheme 7a for the synthesis of a bis carbonate wherein $R_4$ is different than $R_5$.

Schemes 7a and 7b.
Synthesis of Benzylic/Primary Alcohol Bis-Carbonate Prodrugs of Chloroamphenicol Type (Dihydroxyfenicol) with Different Carbonate Moieties at Benzylic and Primary Alcohol Functionalities As illustrated by FIG. 7A, preparation of benzylic/primary alcohol bis-carbonate prodrugs of chloroamphenicol-type (dihydroxyfenicol) with different carbonate moieties at benzylic and primary alcohol functionalities can be achieved as shown in Scheme 7a using benzylic mono-carbonates (compound 6), obtained by methods A-C described above, and subjecting them to a second reaction with chloroformate Cl—(O)C—O—R$_5$(R$_4$≠R$_5$) or with a X—(O)C—O—R$_5$(R$_4$≠R$_5$) reagent of the type described above with relation to Scheme 6.

Figure 7B:
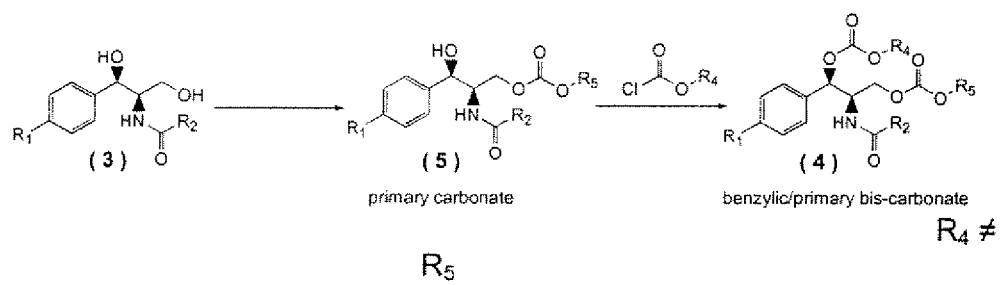
FIG. 7b illustrates reaction scheme 7b for an alternative synthesis of a bis carbonate wherein $R_4$ is different than $R_5$.

Alternatively the desired carbonate prodrug functionality can be introduced first at the primary alcohol functionality and the resulting primary alcohol carbonate intermediate (compound 5) can be further reacted with chloroformate Cl—(O)C—O—R$_4$(R$_4$≠R$_5$) or by reaction with a X—(O)C—O—R$_4$(R$_4$≠R$_5$) reagent of the type described above with relation to Scheme 6 to obtain the desired benzylic/primary alcohol bis-carbonate prodrug (illustrated by FIG. 7B, preparation Scheme 7b ). This particular synthetic scheme may conveniently take advantage of the expected higher reactivity of the primary alcohol functionality.

Methods of Using Inventive Compounds

The present invention also provides methods for administering prophylactically-effective amounts, for preventing, i.e., prophylaxis, and/or for metaphylaxis, as a need and/or the practice merits, and/or for the treatment of infections, e.g., bacterial infections, that can be prevented and/or treated etc., by the antibiotic agent or agents released by the inventive compounds, in vivo. The animal to be so protected or treated is preferably, but not exclusively, a vertebrate, and more preferably a mammal, *avian* or fish. Any of the inventive compounds, or a suitable combination of such compounds, may be administered to the animal subject. Appropriate animal subjects include those in the wild, livestock (e.g., raised for meat, milk, butter, eggs, fur, leather, feathers and/or wool), beasts of burden, research animals, companion animals, as well as those raised for/in zoos, wild habitats and/or circuses.

In a particular embodiment, the animal subject is a mammal. Mammals to be treated include primates, e.g., monkeys, great apes and optionally, humans. Other mammalian subjects *bovine* (e.g., cattle or dairy cows), *porcine* (e.g., hogs or pigs), *ovine* (e.g., goats or sheep), *equine* (e.g., horses), *canine* (e.g., dogs), *feline* (e.g., house cats), camels, deer, antelopes, rabbits, guinea pigs and rodents (e.g., squirrels, rats, mice, gerbils, and hamsters), *cetaceans* (whales, dolphins, porpoise), *pinnipeds* (seals, walrus). *Avians* include Anatidae (e.g., swans, ducks and geese), Columbidae (e.g., doves and pigeons), Phasianidae (e.g., partridges, grouse and turkeys) Thesienidae (e.g., domestic chickens), *Psittacines* (e.g., parakeets, macaws, and parrots), game birds, and ratites, (e.g., ostriches).

Birds treated or protected by the inventive compounds can be associated with either commercial or noncommercial aviculture. These include e.g., Anatidae, such as swans, geese, and ducks, Columbidae, e.g., doves and pigeons, such as domestic pigeons, Phasianidae, e.g., partridge, grouse and turkeys, Thesienidae, e.g., domestic chickens, *Psittacines*, e.g., parakeets, macaws, and parrots, e.g., raised for the pet or collector market, among others.

For purposes of the present invention, the term "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae family, the Serranidae family, the Sparidae family, the Cichlidae family, the Centrarchidae family, the three-Line Grunt (*Parapristipoma trilineatum*), and the Blue-Eyed Plecostomus (*Plecostomus* spp), among others.

Further, examples of potential fish recipients include the Salmonidae family, the Serranidae family, the Sparidae family, the Cichlidae family, the Centrarchidae family, the three-Line Grunt (*Parapristipoma trilineatum*), and the Blue-Eyed Plecostomus (*Plecostomus* spp). Additional fish to be treated with the inventive compound are listed, simply for illustration purposes, by the following table

| TAXON NAME | COMMON NAME |
|---|---|
| *Salmonidae* Family | |
| *Coregonus clupeaformis* | Lake whitefish |
| *Coregonus hoyi* | Bloater |
| *Oncorhynchus keta* | Chum salmon |
| *Oncorhynchus gorbuscha* | Pink salmon |
| *Oncorhynchus kisutch* | Coho salmon (silver salmon) |
| *Oncorhynchus masou* | cherry salmon (masou salmon) |
| *Oncorhynchus nerka* | Sockeye salmon |
| *Oncorhynchus tshawytscha* | (chinook salmon) |
| *Prosopium cylindraceum* | Round whitefish |
| *Oncorhynchus clarki* | Cutthroat trout |
| *Oncorhynchus mykiss* | Rainbow trout |
| *Salmo salar* | Atlantic salmon |
| *Salmo trutta* | Brown trout |
| *Salmo trutta* X *S. fontinalis* | Tiger hybrid-trout |

-continued

| TAXON NAME | COMMON NAME |
|---|---|
| Salvelinus alpinus | Arctic charr |
| Salvelinus confluentus | Bull trout |
| Salvelinus fontinalis | Brook trout |
| Salvelinus leucomaenis | Japanese charr (white spotted charr) |
| Salvelinus malma | Dolly varden (Miyabe charr) |
| Salvelinus namaycush | Lake trout |
| Thymallus thymallus | Grayling |
| Some Members of the *Serranidae* Family | |
| Centropristis ocyurus | Bank sea bass |
| Centropristis philadelphicus | Rock sea bass |
| Centropristis striata | Black sea bass |
| Diplectrum bivittatum | Dwarf sandperch |
| Diplectrum formosum | Sand perch |
| Epinephelus flavolimbatus | Yellowedge grouper |
| Epinephelus morio | Red grouper |
| Serranus phoebe | Tattler |
| Serranus tortugarum | Chalk bass |
| Some Members of the *Sparidae* family | |
| Archosargus probatocephalus | Sheepshead |
| Archosargus rhomboidalis | Sea bream |
| Calamus penna | Sheepshead porgy |
| Lagodon rhomboides | Pinfish |
| Pagrus Major | Red Sea bream |
| Sparus aurata | Gilthead Sea bream |
| Stenotomus chrysops | Scup |
| Some Members of the *Cichlidae* family | |
| Aequidens latifrons | Blue acara |
| Cichlisoma nigrofasciatum | Congo cichlid |
| Crenichichla sp. | Pike cichlid |
| Pterophyllum scalare | Angel fish |
| Tilapia mossambica | Mozambique mouth breeder |
| Oreochromis spp. | Tilapia |
| Sarotherodon aurea | Golden Tilapia |
| Some Members of the *Centrarchidae family* | |
| Ambloplites rupestris | Rock bass |
| Centrarchus macropterus | Flier |
| Elassoma evergladei | Everglades pigmy sunfish |
| Elassoma okefenokee | Okefenokee pigmy sunfish |
| Elassoma zonatum | Banded pigmy sunfish |
| Enneacanthus gloriosus | Bluespotted sunfish |
| Enneacanthus obesus | Banded sunfish |
| Lepomis auritus | Redbreast sunfish |
| Lepomis cyanellus | Green sunfish |
| Lepomis cyanellus X L. gibbosus | Green x pumpkinseed |
| Lepomis gibbosus | Pumpkinseed |
| Lepomis gulosus | Warmouth |
| Lepomis humilis | Orange-spotted sunfish |
| Lepomis macrochirus | Bluegill |
| Lepomis megalotis | Longear sunfish |
| Micropterus coosae | Shoal bass |
| Micropterus dolomieui | Smallmouth bass |
| Micropterus punctulatus | Spotted bass |
| Micropterus salmoides | Largemouth bass |
| Pomoxis annularis | White crappie |
| Pomoxis nigromaculatus | Black crappie |

Still further examples of fish that can be treated include, but are not limited to catfish, sea bass, tuna, halibut, arctic charr, sturgeon, turbot, flounder, sole, carp, tilapia, striped bass, eel, sea bream, yellowtail, amberjack, grouper and milkfish.

Other animals are also contemplated to benefit from the inventive methods, including marsupials (such as kangaroos), reptiles (such as farmed turtles), crustaceans (such as lobsters, crabs, shrimp and prawns) mollusks (such as octopus and shellfish) and other economically important animals for which the inventive methods are safe and/or effective in treating and/or preventing infection.

In another embodiment, the subject is a companion animal. For purposes of the present invention, the term "companion" animal shall be understood to include housecats (*feline*), dogs (*canine*), rabbit species, horses (*equine*), guinea pigs, rodents (e.g., squirrels, rats, mice, gerbils, and hamsters), primates (e.g., monkeys) and *avians*, such as pigeons, doves, parrots, parakeets, macaws, canaries, and the like.

Pharmaceutical Compositions

A compound of the present invention, or a physiologically acceptable solvate of the compound, may be administered as such to an animal in need thereof, or may be administered in pharmaceutical compositions in which the foregoing materials are mixed with suitable excipient(s). Techniques for formulation and administration of drugs may be found in *Remington's Pharmacological Sciences*, Mack Publishing Co., Easton, Pa., latest edition. The formulations and techniques discussed in Remington relate primarily to use with human patients; however, they readily may be modified for use with non-human patients by techniques well-known to those skilled in the veterinary art.

When the inventive compounds described herein are administered as a component of the feed of the animals, or dissolved or suspended in the drinking water, compositions are provided in which the active agent(s) are intimately dispersed in an inert carrier or diluent. An inert carrier is one that will not react with the inventive compound and one that may be administered safely to animals. Preferably, a carrier for feed administration is one that is, or may be, an ingredient of the animal ration.

Suitable compositions include feed pre-mixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone, and the like. The inventive compound is intimately dispersed throughout the carrier by methods such as grinding, stirring, milling or tumbling. Compositions containing from about 0.05 to about 5.0%, or from about 0.005 to about 2.0% by weight of the inventive compounds are particularly suitable as feed pre-mixes. Feed supplements, which are fed directly to the animal contain from about 0.0002 to 0.3% by weight of the inventive compound.

Such supplements are added to the animal feed in an amount to give the finished feed the concentration of active compound desired for the treatment and control of susceptible microorganisms. Although the desired concentration of the inventive compound will vary depending upon the factors mentioned supra as well as upon the particular derivative employed, the compound is usually fed at concentrations of between about 0.0001 to 0.02% or from about 0.00001 to about 0.002% in the feed in order to achieve the desired antimicrobial result.

Routes of Administration

As used herein, "administer" or "administration" refers to the delivery of the compound or solvate of the present invention or of a pharmaceutical composition containing a compound of this invention to an organism for the purpose of treating or preventing a microbial infection.

Suitable routes of administration may include, without limitation, oral, rectal, topical, transmucosal, intramuscular, subcutaneous, intramedullary, intrathecal, direct intraventricular, intravenous, intravitreal, intraperitoneal, intranasal, aural or intraocular. The preferred routes of administration are oral and parenteral.

Alternatively, one may administer the compound in a local rather than systemic manner, for example, by preparation as a salve or topically applied formulation that is applied directly to the infected area or by injection of the compound directly into infected tissue. In either case, a sustained release formulation may be used.

Thus, administration of the compounds of the invention, or their pharmaceutically acceptable solvates, in pure form or in an appropriate pharmaceutical composition, can be carried out via any of the accepted modes of administration or agents for serving similar utilities. The routes of administration can be any known to those of ordinary skill. The inventive compounds are given to those in need thereof in any art recognized form, i.e. solid, semi-solid, lyophilized powder, or liquid dosage forms, such as for example, tablets, suppositories, pills, soft elastic and hard gelatin capsules, powders, solutions, suspensions, or aerosols, or the like, in unit or multi-dosage forms suitable for simple administration of precise dosages. The compositions will include a conventional pharmaceutical carrier or excipient and a compound of the invention as the active agent, and, in addition, may include other medicinal agents, pharmaceutical agents, carriers, adjuvants, etc.

Composition/Formulations

Pharmaceutical compositions of the present invention may be manufactured by processes well known in the art, e.g., using a variety of well-known mixing, dissolving, granulating, dragee-making, levigating, emulsifying, encapsulating, entrapping or lyophilizing processes. The compositions may be formulated in conjunction with one or more physiologically acceptable carriers comprising excipients and auxiliaries which facilitate processing of the active compounds into preparations which can be used pharmaceutically. Proper formulation is dependent upon the route of administration chosen.

For injection, including, without limitation, intravenous, intramuscular and subcutaneous injection, the compounds of the invention may be formulated in polar solvents including, without limitation, propylene glycol, alcohols, such as benzyl alcohol or ethanol, polyethylene glycol, and N-methyl-2-pyrrolidone, 2-pyrrolidone, other pyrrolidones, N,N-dimethylacetamide, N,N-dimethylformamide, dimethylsulfoxide, acetone, triacetin, glycerol formal, optional water at concentrations up to 10%, as well as combinations of any of the foregoing excipients or other materials known to those of ordinary skill. For transmucosal administration, penetrants appropriate to the barrier to be permeated are used in the formulation. Such penetrants are generally known in the art.

Dosage

A therapeutically effective amount refers to an amount of compound effective to prevent and/or minimize microbial infection, and/or treat, alleviate and/or ameliorate symptoms due to a microbial infection. Determination of a therapeutically effective amount is well within the capability of those skilled in the art, especially in light of the disclosure herein.

For any compound used in the methods of the invention, the therapeutically effective amount can be estimated initially from known properties of the antibiotic agent that is released by the inventive prodrug compounds. Then, the dosage can be formulated for use in animal models so as to achieve a circulating concentration range that is at or greater than the minimum inhibitory concentration ("MIC") as previously known to the art. Such information can then be used to more accurately determine dosages useful in patients.

Toxicity and therapeutic efficacy of the compounds described herein can be determined by standard pharmaceutical procedures in cell cultures or experimental animals. For example, the minimum inhibitory concentration ("MIC") and the lethal dose for 50% of a treated group ("$LD_{50}$") for a particular compound can be determined by methods well-known in the art. For instance, MIC is determined according to the guidelines laid down by the Clinical and Laboratory Standards Institiute (CLSI)"

The data obtained can be used to formulate a range of dosages useful in patients. The dosage, of course, may vary depending upon the dosage form and route of administration. The exact formulation, route of administration and dosage can be selected by the individual clinician in view of the patient's condition. (See e.g., Fingl, et al., 1975, in "*The Pharmacological Basis of Therapeutics*", Ch. 1 p. 1). Broadly, the inventive compounds are administered to an animal in need of such treatment in a dose effective to reach and/or maintain concentrations of released antibiotic in plasma and body tissues at levels effective for the purpose, whether to treat and eliminate susceptible infectious microorganisms or to prevent new infection, for a sufficient time period to accomplish the desired goal. The skilled artisan will appreciate that the following estimated dose ranges are adjustable based on clinical response, as well as accounting for the relative amount of the fenicol antibiotic release from each respective prodrug compound, as well as for the molar ratio of fenicol per prodrug (mono versus bis) carbonate compounds. For example, for subcutaneous administration, the inventive compounds are generally administered at a dose ranging from about 1 mg to about 150 mg/kg of body weight. Frequency of administration can also range from a single dose per day to multiple doses per day. For oral administration, the dose will preferably be administered once per day.

Dosage amount and interval may be adjusted individually to provide plasma levels of the compound that are sufficient to maintain a concentration above or equal to the MIC or any other desired level. Such plasma levels are often referred to as minimum effective concentrations (MECs). The MEC will vary for each compound but can be estimated from in vitro data, e.g., the concentration necessary to achieve greater than 80% inhibition of a microbial population. The MEC may be ascertained using the assays described herein. Dosages necessary to achieve the MEC will depend on the individual characteristics of the compound and/or on the animal and/or route of administration. HPLC assays or bioassays can be used to determine plasma concentrations of the compound and/or its corresponding active product.

Dosage intervals can also be determined using MEC value. Compounds should be administered using a regimen that maintains plasma levels above the MEC for 10-90% of the time.

In cases of local administration or selective uptake, the effective local concentration of the drug may not be related to plasma concentration and other procedures known in the art may be employed to determine the correct dosage amount and interval.

The compositions may be administered once daily or divided into multiple doses. Often only one dose will be sufficient to treat the infection. In some circumstances one dose followed by a second dose 48 hours later will be required to treat the animal. The precise dose will depend on the stage and severity of the infection, the susceptibility of the infecting organism to the composition, and the individual characteristics of the animal species being treated, as will be appreciated by one of ordinary skill in the art.

The amount of a composition administered will, of course, be dependent on the patient being treated, pathogen or bacteria causing the infection, the severity of the infection, the manner of administration, i.e., oral, intravenous, topical, etc., and the judgment of the prescribing physician, veterinarian, etc.

The inventive compound will generally be administered at a dose ranging from about 1 mg to about 150 mg/kg body weight in catle, when using the subcutaneous route. Preferably, the dose ranges from about 20 mg to about 70 mg/kg body weight. More preferably, the dose is about 60 mg/kg. However, when the inventive compound is administered via the intra-muscular (IM) route, the dose is preferably administered twice, with the administration of the second dose being about 24 to about 48 hours after the administration or the first dose.

In swine, the inventive compound will generally be administered in a dose ranging from about 10 mg to about 150 mg/kg body weight. Preferably the dose ranges from about 20 mg to 70 mg/kg body weight. Generally, the first intramuscular injection will be followed by a second injection about 24 to about 48 hours later.

In poultry, the inventive compound will generally be administered in a dose ranging from about 10 mg to 150 mg/kg body weight. Orally, the prodrug will be administered in drinking water daily, for as long as is clinically indicated, e.g., for from about three to about seven days.

Administration to Aquatic Animals

The present invention also provides methods of eliminating, reducing or preventing bacterial infections in fish, and optionally aquatic invertebrates. Such methods include administering an effective amount of an inventive compound of the invention to the aquatic animal in need thereof. Administering generally is achieved by either feeding the animal an effective amount of the inventive compound or by immersing the animal or animal population in a solution which contains an effective amount of the active compound in solution. It is to be further understood that the inventive compound can be administered by application of the drug to a pool or other water-holding area containing the animal, and allowing the animal to absorb the compound through their gills or otherwise allowing the dosage of the inventive compound to be taken in. For individual treatment of specific animals, such as a particular fish, e.g., in a veterinary or aquarium setting, direct injection or injection of osmotic release devices comprising the inventive compound, alone or in combination with other agents, is an optional method of administering the inventive compound.

The dose of the inventive compounds that is effective for reducing, eliminating, or preventing the bacterial infection in fish or other aquatic species can be routinely determined by a veterinarian using the parameters and methods discussed supra for other types of animals, although it may vary depending on the species of fish treated, the particular microorganisms involved, and the degree of infection. For aquaculture indications, the inventive compounds will generally be administered at a dosage of about 1 mg/kg to about 70 mg/kg, and preferably from 10 mg/kg to 30 mg/kg. Suitable routes of administering include: intravenously, subcutaneously, intramuscularly and/or by spraying or dipping the aquatic species as needed, and/or by directly adding the compound into the water in a holding volume.

For oral administration, the inventive compounds are preferably administered at the doses specified above from about 10 to about 15 days.

While the active ingredient can be administered separately from food, it is contemplated that in a preferred aspect that the active will be incorporated into the fish feed. A medicated fish feed may be prepared by incorporating a suitable amount of compound of the present invention into a commercially available fish feed product to achieve the desired dosing levels. The amount of compound of the present invention incorporated into the fish feed will depend on the rate at which the fish are fed. For fish fed at the rate of about 0.2% to 4% of biomass/day, the medicated feed preferably contains from about 50 to 10,000 mg per kg of feed, and more preferably, from about 100 to 2,000 mg per kg of feed.

Although compounds of the present invention can be incorporated into a feed mixture prior to pelleting, the medicated feed is preferably formed by coating feed pellets with compound of the present invention.

Any fish species, including fresh water and salt water varieties, as well as invertebrate aquatic species, an enumerated hereinabove, can be treated with the compounds of the present invention to treat or prevent bacterial infections.

Combinations with Other Agents and Treatment Modalities

It is also contemplated to administer the inventive prodrug compounds in combination, simultaneously, or sequentially (e.g. in the same composition or in separate compositions) with other useful art-known medicinal agents. Such medicinal agents include, e.g., other microbiocides, e.g., antibiotics, antifungals, antivirals, parasiticides, and so forth, as well as in nutritional supplements, feed additives and the like. For example, it is contemplated to administer any art-known standard (non-prodrug) fenicol in combination with the inventive compounds. Such fenicols include florfenicol, also known as D-(threo)-1-(4-methylsulfonylphenyl)-2-dichloroacetamido-3-fluoro-1-propanol. Another preferred antibiotic compound is D-(threo)-1-(4-methylsulfonyphenyl)-2-difluoroacetamido-3-fluoro-1-propanol. Another useful antibiotic is thiamphenicol. Processes for the manufacture of these antibiotic compounds, and intermediates useful in such processes, are described in U.S. Pat. Nos. 4,311,857; 4,582,918; 4,973,750; 4,876,352; 5,227,494; 4,743,700; 5,567,844; 5,105,009; 5,382,673; 5,352,832; and 5,663,361, hereby incorporated by reference. Other florfenicol analogs and/or prodrugs have been disclosed and such analogs also can be used in the compositions and methods of the present invention [see e.g., U.S. Patent Application Publication No: 2004/0082553, and U.S. Patent Application Publication No. 2005/0182031, both of which are hereby incorporated by reference in their entireties]. When the antibiotic compound is florfenicol, the concentration of florfenicol typically is from about 10% to about 50% w/v, with the preferred level between about 20% and about 40% w/v, even more preferred being at least about 30% w/v.

Another useful antibiotic compound for use in a combination with the inventive compounds is tilmicosin. Tilmicosin is a macrolide antibiotic that is chemically defined as 20-dihydro-20-deoxy-20-(cis-3,5-dimethylpiperidin-1-yl)-desmycosin and which is reportedly disclosed in U.S. Pat. No. 4,820,695, hereby incorporated by reference. Also disclosed in U.S. Pat. No. 4,820,695 is an injectable, aqueous formulation comprising 50% (by volume) propylene glycol, 4% (by volume) benzyl alcohol, and 50 to 500 mg/ml of active ingredient. Tilmicosin may be present as the base or as a phosphate. Tilmicosin has been found to be useful in treatment of respiratory infections, particularly *Pasteurella haemolytica* infections in cattle when administered by injection over a 4 day treatment period. Accordingly, tilmicosin may be used in treatment of, for example, neonatal calf pneumonia and bovine respiratory disease. When tilmicosin is present, it is present in an amount of about 1% to about 50%, preferably 10% to about 50%, and in a particular embodiment, 30%.

Another useful antibiotic for use in combination with the inventive compounds is tulathromycin. Tulathromycin may be prepared in accordance with the procedures set forth in U.S. Patent Publication No. 2003/0064939 A1, which is hereby incorporated by reference in its entirety. Tulathromycin may be present in injectable dosage forms at concentration levels ranging from about 5.0% to about 70% by weight. Tulathromycin is most desirably administered in dosages ranging from about 0.2 mg per kg body weight per day (mg/kg/day) to about 200 mg/kg/day in single or divided doses (i.e., from 1 to 4 doses per day), and more preferably 1.25, 2.5 or 5 mg/kg once or twice weekly, although variations will necessarily occur depending upon the species, weight and condition of the subject being treated. Tulathromycin may be present in injectable dosage forms at concentration levels ranging from about 5.0% to about 70% by weight.

Another useful antibiotic for use in combination with the inventive compounds is the fluoroquinolones family of antibiotics, such as, for example, enrofloxacin, danofloxacin, difloxacin, orbifloxacin and marbofloxacin. In the case of enrofloxacin, it may be administered in a concentration of about 100 mg/ml. danofloxacin may be present in a concentration of about 180 mg/ml.

Other useful macrolide antibiotics for use in combination with the inventive compounds include compounds from the class of ketolides, or, more specifically, the azalides. Such compounds are described in, for example, U.S. Pat. Nos. 6,514,945, 6,472,371, 6,270,768, 6,437,151 and 6,271,255, and U.S. Pat. Nos. 6,239,112, 5,958,888, and U.S. Pat. Nos. 6,339,063 and 6,054,434, all of which are hereby incorporated by reference in their entireties.

Other useful antibiotics for use in combination with the inventive compounds include the tetracyclines, particularly chlortetracycline and oxytetracycline.

Other antibiotics may include beta-lactams such as one of the penicillins, e.g., penicillin G, penicillin K, ampicillin, amoxicillin, or a combination of amoxicillin with clavulanic acid or other beta-lactamase inhibitors. Additional particular beta-lactams include the cephalosporins such as, for example, ceftiofur, cefquinome, etc. The concentration of the cephalosporin in the formulation of the present invention optionally varies between about 1 mg/ml to 500 mg/ml.

Additionally, the present invention optionally includes a composition for the treatment of a microbial and parasitic infection in an animal that comprises one or more of the above-listed antibiotics admixed and/or in combination with one or more of the inventive compounds, and an optional carrier and/or excipient.

For all of the methods and the inventive compounds described herein, it is also contemplated that the identified compounds are readily employed in combination with one or more art-known agents for killing or controlling various types of parasites, e.g., including all of the ecto- and endoparasites described herein. Thus, although the inventive compounds and methods are preferred over previously known agents and methods of using previously known agents, in certain optional embodiments they are contemplated to be employed in combination, simultaneously, or sequentially (e.g. in the same composition or in separate compositions), with other art-known agents or combinations of such art-known agents employed for killing or controlling various types of pests.

These additional agents for use in combination with the inventive compounds include, for example, art-known anthelmintics, such as, for example, avermectins (e.g. ivermectin, moxidectin, milbemycin), benzimidazoles (e.g. albendazole, triclabendazole), salicylanilides (e.g. closantel, oxyclozanide), substituted phenols (e.g. nitroxynil), pyrimidines (e.g. pyrantel), imidazothiazoles (e.g. levamisole) and praziquantel.

Additional art-known agents for killing or controlling pests for use in combination with the inventive compounds include the organophosphate pesticides. This class of pesticides has very broad activity, e.g. as insecticides and, in certain instances, anthelminitic activity. Organophosphate pesticides include, e.g., dicrotophos, terbufos, dimethoate, diazinon, disulfoton, trichlorfon, azinphos-methyl, chlorpyrifos, malathion, oxydemeton-methyl, methamidophos, acephate, ethyl parathion, methyl parathion, mevinphos, phorate, carbofenthion, phosalone, to name but a few such compounds. It is also contemplated to include combinations of the inventive methods and compounds with carbamate type pesticides, including, e.g., carbaryl, carbofuran, aldicarb, molinate, methomyl, etc., as well as combinations with the organochlorine type pesticides. It is further contemplated to include combinations with biological pesticides, including e.g. repellents, the pyrethrins (as well as synthetic variations thereof, e.g., allethrin, resmethrin, permethrin, tralomethrin), and nicotine, that is often employed as an acaricide. Other contemplated combinations are with miscellaneous pesticides including: *Bacillus thuringiensis*, chlorobenzilate, formamidines, (e.g. amtitaz), copper compounds, e.g., copper hydroxide, cupric oxychloride sulfate, cyfluthrin, cypermethrin, dicofol, endosulfan, esenfenvalerate, fenvalerate, lambda-cyhalothrin, methoxychlor and sulfur.

In addition, for all of the methods and new compounds described herein, it is further contemplated that the identified compounds can be readily employed in combination with syngergists such as piperonyl butoxide (PBO) and triphenyl phosphate (TPP); and/or with Insect Growth Regulators (IGRs) and Juvenile Hormone Analogues (JHAs) such as diflubenzuron, cyromazine, methoprene, etc., thereby providing both initial and sustained control of parasites (at all stages of insect development, including eggs) on the animal subject, as well as within the environment of the animal subject.

Combinations with cyclodienes, ryania, KT-199 and/or older art-known antihelminthic agents, such as avermectins (e.g., ivermectin, moxidectin, milbemycin), benzimidazoles (e.g., albendazole, triclabendazole), salicylanilides (e.g., closantel, oxyclozanide), substituted phenols (e.g., nitroxynil), pyrimidines (e.g., pyrantel), imidazothiazoles (e.g., levamisole), praziquantel and some organophosphates such as naphthalophos and pyraclofos, are also contemplated to be employed in such combinations.

In particular, additional antiparasitic compounds useful within the scope of the present invention are preferably comprised of the class of avermectin compounds. As stated above, the avermectin family of compounds is a series of very potent antiparasitic agents known to be useful against a broad spectrum of endoparasites and ectoparasites in mammals.

A preferred compound for use in combination with the inventive compounds within the scope of the present invention is ivermectin. Ivermectin is a semi-synthetic derivative of avermectin and is generally produced as a mixture of at least 80% 22,23-dihydroavermectin $B1_a$ and less than 20% 22,23-dihydroavermectin $B1_b$. Ivermectin is disclosed in U.S. Pat. No. 4,199,569, hereby incorporated by reference. Ivermectin has been used as an antiparasitic agent to treat various animal parasites and parasitic diseases since the mid-1980's.

Abamectin is an avermectin that is disclosed as avermectin B1a/B1b in U.S. Pat. No. 4,310,519, which is hereby incorporated by reference in its entirety. Abamectin contains at least 80% of avermectin $B1_a$ and not more than 20% of avermectin $B1_b$.

Another preferred avermectin is doramectin also known as 25-cyclohexyl-avermectin $B_1$. The structure and preparation of doramectin, is disclosed in U.S. Pat. No. 5,089,480, which is hereby incorporated by reference in its entirety.

Another preferred avermectin is moxidectin. Moxidectin, also known as LL-F28249 alpha is known from U.S. Pat. No. 4,916,154, which is hereby incorporated by reference in its entirety.

Another preferred avermectin is selamectin. Selamectin is 25-cyclohexyl-25-de(1-methylpropyl)-5-deoxy-22,23-dihydro-5-(hydroxyimino)-avermectin $B_1$ monosaccharide.

Milbemycin, or B41, is a substance which is isolated from the fermentation broth of a milbemycin producing strain of *Streptomyces*. The microorganism, the fermentation conditions and the isolation procedures are more fully described in U.S. Pat. No. 3,950,360 and U.S. Pat. No. 3,984,564.

Emamectin (4"-deoxy-4"-epi-methylaminoavermectin $B_1$), which can be prepared as described in U.S. Pat. No. 5,288,710 or U.S. Pat. No. 5,399,717, is a mixture of two homologues, 4"-deoxy-4"-epi-methylaminoavermectin B1a and 4"-deoxy-4"-epi-methylaminoavermectin B1b. Preferably, a salt of emamectin is used. Non-limiting examples of salts of emamectin which may be used in the present invention include the salts described in U.S. Pat. No. 5,288,710, e.g., salts derived from benzoic acid, substituted benzoic acid, benzenesulfonic acid, citric acid, phosphoric acid, tartaric acid, maleic acid, and the like. Most preferably, the Emamectin salt used in the present invention is emamectin benzoate.

Eprinomectin is chemically known as 4"-epi-Acetylamino-4"-deoxy-avermectin $B_1$. Eprinomectin was specifically developed to be used in all cattle classes and age groups. It was the first avermectin to show broad-spectrum activity against both endo- and ecto-parasites while also leaving minimal residues in meat and milk. It has the additional advantage of being highly potent when delivered topically.

The composition of the present invention optionally comprises combinations of one or more of the following antiparasite compounds.

The antiparasite imidazo[1,2-b]pyridazine compounds as described by U.S. Patent Application Publication No: 2005/0182059, incorporated by reference herein. The antiparasite 1-(4-mono and di-halomethylsulphonylphenyl)-2-acylamino-3-fluoropropanol compounds, as described by U.S. Patent Application Publication No: 2005/0182139, incorporated by reference herein. The antiparasite trifluoromethanesulfonanilide oxime ether derivative compounds, as described by U.S. Patent Application Publication No: 2006/0063841, incorporated by reference herein. The antiparasite phenyl-3-(1 H-pyrrol-2-yl)acrylonitrile compounds, as described by U.S. Patent Application Publication No: 2006/0128779, incorporated by reference herein. The antiparasite N-[(phenyloxy)phenyl]-1,1,1-trifluoromethanesulfonamide and N-[(phenylsulfanyl)phenyl]-1,1,1-trifluoromethanesulfonamide derivatives, as described by U.S. application Ser. No. 11/448,421, filed on Jun. 7, 2006, incorporated by reference herein. The antiparasite N-phenyl-1,1,1-trifluoromethanesulfonamide hydrazone compounds, as described by U.S. Provisional Application Ser. No. 60/790,893, filed on Apr. 10, 2006, incorporated by reference herein.

The compositions of the present invention may also be employed in combination with a flukicide. Suitable flukicides include, for example, triclabendazole, fenbendazole, albendazole, clorsulon and oxibendazole. It will be appreciated that the above combinations may further include combinations of antibiotic, antiparasitic and anti-fluke active compounds.

In addition to the above combinations, it is also contemplated to provide combinations of the inventive methods and compounds, as described herein, with other animal health remedies such as trace elements, anti-inflammatories, anti-infectives, hormones, dermatological preparations, including antiseptics and disinfectants, and immunobiologicals such as vaccines and antisera for the prevention of disease.

For example, such antinfectives include one or more antibiotics that are optionally co-administered during treatment using the inventive compounds or methods, e.g., in a combined composition and/or in separate dosage forms. Art-known antibiotics suitable for this purpose include, for example, those listed hereinabove.

Further, it is also contemplated that the inventive methods and compounds be advantageously employed in combination, simultaneously or sequentially, with art-known animal health remedies e.g., trace elements, vitamins, anti-inflammatories, anti-infectives and the like, in the same or different compositions.

Suitable anti-inflammatory agents include, e.g., both steroidal and non-steroidal anti-inflammatory agents. Non-steroidal anti-inflammatory agents, including their racemic mixtures or individual enantiomers where applicable, can include ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketorolac, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate.

In a particular embodiment, a compound of the present invention is employed in combination with flunixin, [see, e.g., U.S. Pat. No. 6,790,867 B2, which is hereby incorporated by reference in its entirety.] In a related embodiment, the present invention provides a pharmaceutical composition comprising a compound of the present invention and flunixin.

Steroidal anti-inflammatory agents include, for example, glucocorticoid agents such as dexamethasone, cortisone, hydrocortisone, prednisone, beclomethasone, betamethasone, flunisolide, methyl prednisone, para methasone, prednisolone, triamcinolome, alclometasone, amcinonide, clobetasol, fludrocortisone, diflurosone diacetate, fluocinolone acetonide, fluoromethalone, flurandrenolide, halcinonide, medrysone, mometasone, and pharmaceutically acceptable salts and mixtures thereof.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. In an optional embodiment, the packaging comprises glass or plastic vials or other containers comprising multiple doses.

EXAMPLES

The following examples are provided to illustrate certain embodiments of this invention and are not intended, nor are they to be construed, to limit its scope in any manner whatsoever.

Examples 1-25

Preparation of Florfenicol Carbonate Prodrugs

Synthesis of Carbonate Prodrugs of Florfenicol and its Analogs.

Figure 4:
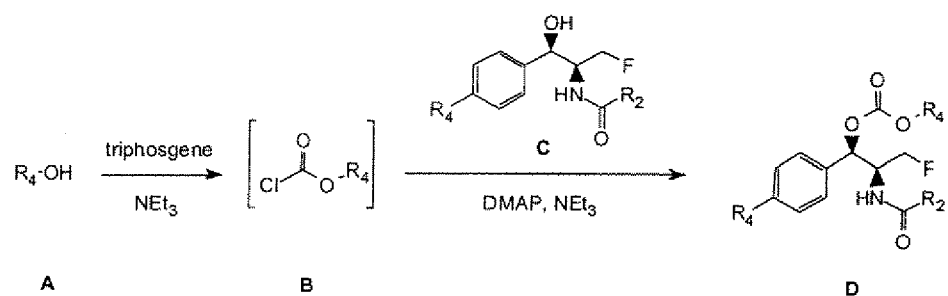
FIG. 4 illustrates the synthesis of fenicol carbonate compound D by reacting starting alcohol A with triethyl amine to provide chloroformate B which is reacted with fenicol C to produce compound D.

With reference to FIG. 4, a solution of the starting alcohol A (0.68 M, 1.78 molar equivalents) and triethyl amine (0.68 M, 1.78 molar equivalents) in anhydrous tetrahydrofuran was added dropwise to a solution of triphosgene (0.48 M, 0.64 molar equivalents) in anhydrous tetrahydrofuran at 0° C. under a nitrogen atmosphere. The resulting mixture was stirred at 0° C. for 30 minutes and then rapidly filtered through a filter paper to remove the ammonium salt. The filtrate solution of the chloroformate solution B was used for the following carbonation reaction without further purification.

The freshly prepared solution of chloroformate B, or an anhydrous tetrahydrofuran solution of the commercially available chloroformate B (0.34 M, 1.78 molar equivalent), was transferred to a dropping funnel and ⅔ of the solution was added dropwise to an anhydrous tetrahydrofuran solution containing corresponding fenicol C (0.64 M, 1 molar equivalent, 4-N,N-dimethylaminopyridine (0.5 molar equivalent), and triethylamine (1.5 molar equivalents) at 0° C. under a nitrogen atmosphere. The mixture was stirred at 0° C. for 30 minutes, and the progress of the reaction was monitored by thin layer chromatography. Additional chloroformate solution was added when the reaction was not completed as indicated by the thin layer chromatography and the reaction was continued until the disappearance of the starting material. The resulting solution was rapidly filtered through a filter paper to remove the ammonium salt. The filtrate was concentrated and ethyl acetate was added to dissolve the crude product. The resulting solution was washed sequentially with 1 M $HCl_{(aq)}$, saturated $NaHCO_{3(aq)}$, and saturated $NaCl_{(aq)}$, followed by a rapid filtration through a pad of silica gel and $Na_2SO_4$. The filtrate was concentrated and the crude product obtained was purified by flash silica gel column chromatography or recrystallization (using the solvents listed by Table 5) to give the pure carbonate prodrug D. The following compounds, by example number, were obtained by the above method:

TABLE 2

| Example No. | Compound Name |
|---|---|
| 1 | (1R,2S)-2-(2,2-dichloroacetamido)-3-fluoro-1-(4-(methylsulfonyl)phenyl)propyl methyl carbonate. |
| 2 | (1R,2S)-2-(2,2-dichloroacetamido)-3-fluoro-1-(4-(methylsulfonyl)phenyl)propyl ethyl carbonate. |
| 3 | (1R,2S)-2-(2,2-dichloroacetamido)-3-fluoro-1-(4-(methylsulfonyl)phenyl)propyl propyl carbonate. |
| 4 | (1R,2S)-2-(2,2-dichloroacetamido)-3-fluoro-1-(4-(methylsulfonyl)phenyl)propyl isopropyl carbonate. |

TABLE 2-continued

| Example No. | Compound Name |
|---|---|
| 5 | (1R,2S)-2-(2,2-dichloroacetamido)-3-fluoro-1-(4-(methylsulfonyl)phenyl)propyl isobutyl carbonate. |
| 6 | cyclopropylmethyl (1R,2S)-2-(2,2-dichloroacetamido)-3-fluoro-1-(4-(methylsulfonyl)phenyl)propyl carbonate. |
| 7 | (1R,2S)-2-(2,2-dichloroacetamido)-3-fluoro-1-(4-(methylsulfonyl)phenyl)propyl 3-methylbut-2-enyl carbonate. |
| 8 | (1R,2S)-2-(2,2-dichloroacetamido)-3-fluoro-1-(4-(methylsulfonyl)phenyl)propyl isopentyl carbonate. |
| 9 | (1R,2S)-2-(2,2-dichloroacetamido)-3-fluoro-1-(4-(methylsulfonyl)phenyl)propyl pentan-3-yl carbonate. |
| 10 | cyclohexyl (1R,2S)-2-(2,2-dichloroacetamido)-3-fluoro-1-(4-(methylsulfonyl)phenyl)propyl carbonate. |
| 11 | (1R,2S)-2-(2,2-dichloroacetamido)-3-fluoro-1-(4-(methylsulfonyl)phenyl)propyl 2-methoxyethyl carbonate. |
| 12 | (1R,2S)-2-(2,2-dichloroacetamido)-3-fluoro-1-(4-(methylsulfonyl)phenyl)propyl 2-ethoxyethyl carbonate. |
| 13 | (1R,2S)-2-(2,2-dichloroacetamido)-3-fluoro-1-(4-(methylsulfonyl)phenyl)propyl 2-butoxyethyl carbonate |
| 4 | benzyl (1R,2S)-2-(2,2-dichloroacetamido)-3-fluoro-1-(4-(methylsulfonyl)phenyl)propyl carbonate. |
| 15 | (1R,2S)-2-(2,2-dichloroacetamido)-3-fluoro-1-(4-(methylsulfonyl)phenyl)propyl 4-methylbenzyl carbonate. |
| 16 | (1R,2S)-2-(2,2-dichloroacetamido)-3-fluoro-1-(4-(methylsulfonyl)phenyl)propyl 4-methoxybenzyl carbonate. |
| 17 | (S)-ethyl 2-(1R,2S)-2-(2,2-dichloroacetamido)-3-fluoro-1-(4-(methylsulfonyl)phenyl)propoxy)carbonyloxy)propanoate. |
| 18 | (1R,2S)-2-(2,2-dichloroacetamido)-3-fluoro-1-(4-(methylsulfonyl)phenyl)propyl dodecyl carbonate. |
| 19 | (1R,2S)-2-(2,2-dichloroacetamido)-3-fluoro-1-(4-(methylsulfonyl)phenyl)propyl octadecyl carbonate. |
| 20 | (1R,2S)-2-(2,2-dichloroacetamido)-3-fluoro-1-(4-(methylsulfonyl)phenyl)propyl-(3R,S)-3,7-dimethyloct-6-enyl carbonate. |
| 21 | (1R,2S)-2-(2,2-dichloroacetamido)-3-fluoro-1-(4-(methylsulfonyl)phenyl)propyl 2-(2-methoxyethoxy)ethyl carbonate. |
| 22 | (1R,2S)-2-(2,2-dichloroacetamido)-3-fluoro-1-(4-(methylsulfonyl)phenyl)propyl octyl carbonate. |
| 23 | (1R,2S)-2-(2,2-dichloroacetamido)-3-fluoro-1-(4-(methylsulfonyl)phenyl)propyl 2-(2-(2-methoxyethoxy)ethoxy)ethyl carbonate. |
| 24 | (1R,2S)-1-(4-(6-cyanopyridin-3-yl)phenyl)-2-(2,2-dichloroacetamido)-3-fluoropropyl ethyl carbonate. |
| 25 | (1R,2S)-2-(2,2-dichloroacetamido)-3-fluoro-1-(4-fluoromethylsulfonyl)phenyl)propyl ethyl carbonate. |
| 26 | bis((1R,2S)-2-(2,2-dichloroacetamido)-3-fluoro-1-(4-(methylsulfonyl)phenyl)propyl) ethane-1,2-diyl dicarbonate. |

Example 1

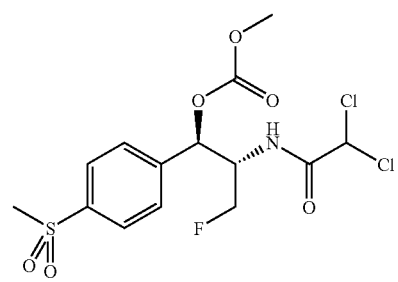

(1R,2S)-2-(2,2-dichloroacetamido)-3-fluoro-1-(4-(methylsulfonyl)phenyl)propyl methyl carbonate The crude product was recrystallized from methanol/water to give 93% yield of the title product as a white solid;

H$^1$-NMR (DMSO-d$_6$), δ=3.2 ppm (s, 3H), 3.70 ppm (s, 3H), 4.3-4.7 ppm (m, 3H), 5.9 ppm (d, 1H), 6.4 ppm (s, 1H), 7.6 ppm (d, 2H), 7.9 ppm (d, 2H), 9.05 ppm (d, 1H); mass spectrum 438.0 (M+Na).

Example 2

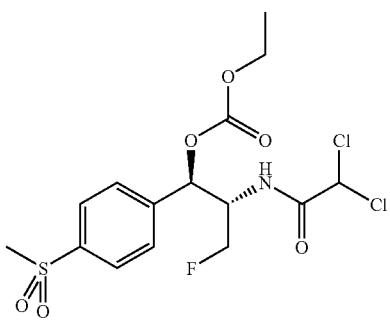

(1R,2S)-2-(2,2-dichloroacetamido)-3-fluoro-1-(4-(methylsulfonyl)phenyl)propyl ethyl carbonate A solution of florfenicol (250 g, 0.7 mol), 4-dimethylaminopyridine (42 g, 0.35 mol,), triethylamine (130 mL, 0.91 mol) in 1.2 L of tetrahydrofuran was stirred at 0-5° C. while neat ethyl chloroformate (80 mL, 0.83 mol) was added dropwise with an addition funnel. The reaction proceeded as indicated by the precipitation of triethylamine hydrochloride salt. The mixture was allowed to stir at room temperature for 30 minutes and the salt was removed from the mixture by filtration. The filtrate was concentrated and 600 mL of ethyl acetate was added and the solution was washed with 1 M HCl (2×200 mL) followed by saturated NaCl (200 mL) and filtered through a layer of Na$_2$SO$_4$/silica gel. The filtrate was concentrated and the crude oil was crystallized from 450 mL of isopropanol to give the pure title product (286 g). m.p. 110-112° C.; H$^1$-NMR (DMSO-d$_6$), δ=1.2 ppm (t, 3 H), 3.2 ppm (s, 3H), 4.1 ppm (q, 2H), 4.3-4.7 ppm (m, 3H), 5.9 ppm (d, 1H), 6.4 ppm (s, 1H), 7.6 ppm (d, 2H), 7.9 ppm (d, 2H), 9.2 ppm (d, 1H); mass spectrum 452.0 (M+Na).

Example 3

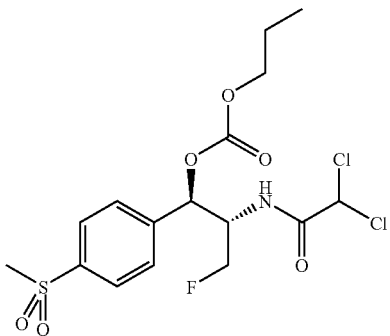

(1R,2S)-2-(2,2-dichloroacetamido)-3-fluoro-1-(4-(methylsulfonyl)phenyl)propyl propyl carbonate The crude product was crystallized from isopropanol to give 91% yield of the title product as a white solid. H$^1$-NMR (DMSO-d$_6$), δ=0.85 ppm (t, 3 H), 1.58 ppm (hex, 2H), 3.2 ppm (s, 3H), 4.1 ppm (t, 2H), 4.3-4.7 ppm (m, 3H), 5.9 ppm (d, 1H), 6.4 ppm (s, 1H), 7.6 ppm (d, 2H), 7.9 ppm (d, 2H), 9.2 ppm (d, 1H); mass spectrum 466.0 (M+Na).

Example 4

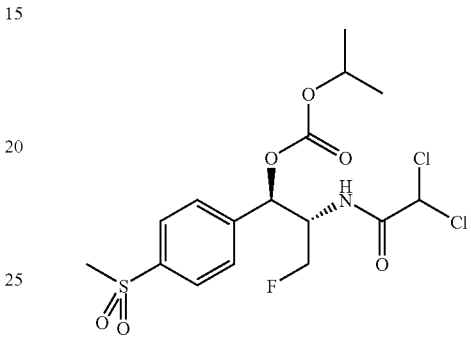

(1R,2S)-2-(2,2-dichloroacetamido)-3-fluoro-1-(4-(methylsulfonyl)phenyl)propyl isopropyl carbonate The crude product was crystallized from isopropanol to give 92% yield of the title product as a white solid. H$^1$-NMR (DMSO-d$_6$), δ=1.2 ppm (2d, 6H), 3.2 ppm (s, 3H), 4.3-4.7 ppm (m, 3H), 4.75 ppm (hep, 1H), 5.9 ppm (d, 1H), 6.4 ppm (s, 1H), 7.6 ppm (d, 2H), 7.9 ppm (d, 2H), 9.0 ppm (d, 1H); mass spectrum 466.0 (M+Na).

Example 5

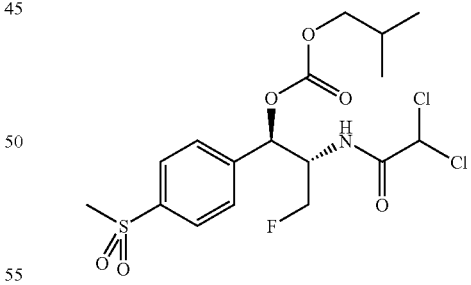

(1R,2S)-2-(2,2-dichloroacetamido)-3-fluoro-1-(4-(methylsulfonyl)phenyl)propyl isobutyl carbonate The crude product was crystallized from isopropanol/ethanol to give 92% yield of the title product as a white solid. H$^1$-NMR (DMSO-d$_6$), δ=0.85 ppm (d, 6H), 1.85 ppm (hep, 1 H), 3.2 ppm (s, 3H), 4.3-4.7 ppm (m, 3H), 5.9 ppm (d, 1H), 6.45 ppm (s, 1H), 7.6 ppm (d, 2H), 7.9 ppm (d, 2H), 9.05 ppm (d, 1H); mass spectrum 480.0 (M+Na).

Example 6

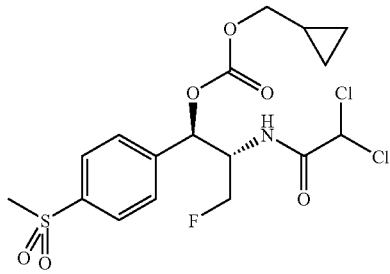

Cyclopropylmethyl(1R,2S)-2-(2,2-dichloroaceta-
mido)-3-fluoro-1-(4-(methylsulfonyl)phenyl)propyl
carbonate The crude product was purified by gel column chromatography and followed by crystallization from ethyl acetate/hexane to give 72% yield of the title product as a white solid. $H^1$-NMR (DMSO-$d_6$), δ=0.25 ppm (dd, 2H), 0.55 ppm (dd, 2H), 1.05 (m, 1H), 3.2 ppm (s, 3H), 3.9 ppm (d, 2H), 4.3-4.7 ppm (m, 3H), 5.9 ppm (d, 1H), 6.45 ppm (s, 1H), 7.6 ppm (d, 2H), 7.9 ppm (d, 2H), 9.05 ppm (d, 1H); mass spectrum 477.9 (M+Na).

Example 7

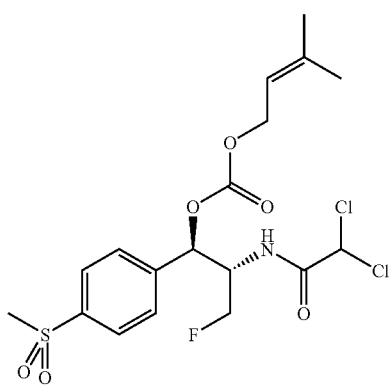

(1R,2S)-2-(2,2-dichloroacetamido)-3-fluoro-1-(4-
(methylsulfonyl)phenyl)propyl 3-methylbut-2-enyl
carbonate The crude product was purified by gel column chromatography to give 80% yield of the title product as a white foam. $H^1$-NMR (DMSO-$d_6$), δ=1.65 ppm (s, 3H), 1.70 ppm (s, 3H), 3.2 ppm (s, 3H), 4.25-4.7 ppm (m, 5H), 5.25 ppm (t, 1H), 5.9 ppm (d, 1H), 6.45 ppm (s, 1H), 7.6 ppm (d, 2H), 7.9 ppm (d, 2H), 9.05 ppm (d, 1H); mass spectrum 491.8 (M+Na).

Example 8

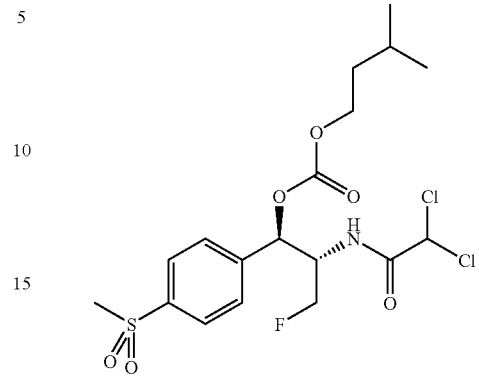

(1R,2S)-2-(2,2-dichloroacetamido)-3-fluoro-1-(4-
(methylsulfonyl)phenyl)propyl isopentyl carbonate The crude product was recrystallized from ethyl acetate/hexane to give 85% yield of the title product as a white solid. $H^1$-NMR (DMSO-$d_6$), δ=0.85 ppm (d, 6H), 1.45 ppm (m, 2H), 1.60 ppm (hep, 1 H), 3.2 ppm (s, 3H), 4.10 ppm (m, 2H), 4.3-4.7 ppm (m, 3H), 5.9 ppm (d, 1H), 6.45 ppm (s, 1H), 7.6 ppm (d, 2H), 7.9 ppm (d, 2H), 9.05 ppm (d, 1H); mass spectrum 494.1 (M+Na).

Example 9

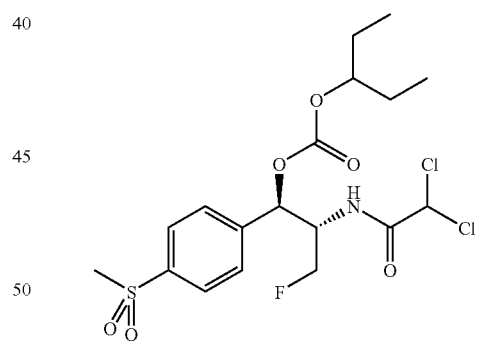

(1R,2S)-2-(2,2-dichloroacetamido)-3-fluoro-1-(4-
(methylsulfonyl)phenyl)propyl pentan-3-yl carbonate The crude product was purified by gel column chromatography to give 73% yield of the title product as a white solid. $H^1$-NMR (DMSO-$d_6$), δ=0.8 ppm (dt, 6H), 1.5 ppm (m, 4H), 3.2 ppm (s, 3H), 4.3-4.7 ppm (m, 4H), 5.95 ppm (d, 1H), 6.45 ppm (s, 1H), 7.6 ppm (d, 2H), 7.9 ppm (d, 2H), 9.05 ppm (d, 1H); mass spectrum 493.9 (M+Na).

Example 10

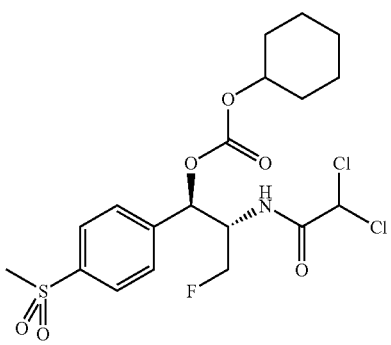

Cyclohexyl(1R,2S)-2-(2,2-dichloroacetamido)-3-fluoro-1-(4-(methylsulfonyl)phenyl)propyl carbonate The crude product was purified by gel column chromatography to give 75% yield of the title product as a white solid. $H^1$-NMR (DMSO-$d_6$), δ=1.1-1.9 ppm (m, 10H), 3.2 ppm (s, 3H), 4.3-4.65 ppm (m, 4H), 5.95 ppm (d, 1H), 6.45 ppm (s, 1H), 7.6 ppm (d, 2H), 7.9 ppm (d, 2H), 9.05 ppm (d, 1H); mass spectrum 505.0 (M+Na).

Example 11

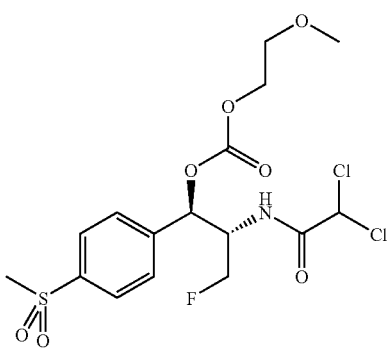

(1R,2S)-2-(2,2-dichloroacetamido)-3-fluoro-1-(4-(methylsulfonyl)phenyl)propyl 2-methoxyethyl carbonate The crude product was purified by gel column chromatography to give 78% yield of the title product as a white semi-solid. $H^1$-NMR (DMSO-$d_6$), δ=3.15 ppm (s, 3H), 3.25 ppm (s, 3H), 3.5 ppm (m, 2H), 4.2 ppm (m, 2H), 4.3-4.7 ppm (m, 3H), 5.95 ppm (d, 1H), 6.45 ppm (s, 1H), 7.6 ppm (d, 2H), 7.9 ppm (d, 2H), 9.05 ppm (d, 1H); mass spectrum 481.9 (M+Na).

Example 12

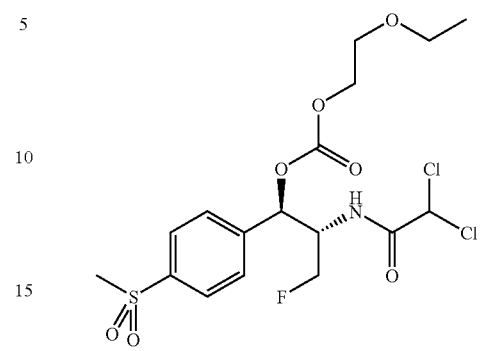

(1R,2S)-2-(2,2-dichloroacetamido)-3-fluoro-1-(4-(methylsulfonyl)phenyl)propyl 2-ethoxyethyl carbonate The crude product was purified by gel column chromatography to give 33% yield of the title product as a white semi-solid. $H^1$-NMR (DMSO-$d_6$), δ=1.05 ppm (t, 3H), 3.15 ppm (s, 3H), 3.4 ppm (q, 2H), 3.55 ppm (m, 2H), 4.2 ppm (m, 2H), 4.3-4.7 ppm (m, 3H), 5.95 ppm (d, 1H), 6.45 ppm (s, 1H), 7.6 ppm (d, 2H), 7.9 ppm (d, 2H), 9.05 ppm (d, 1H); mass spectrum 496.0 (M+Na).

Example 13

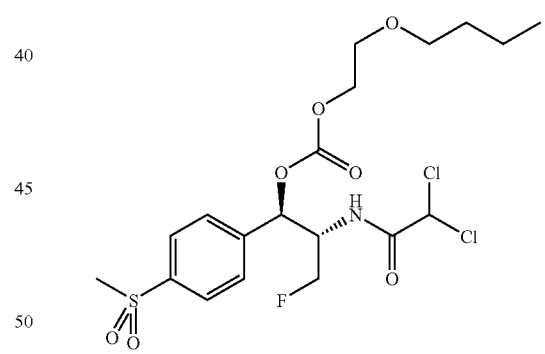

(1R,2S)-2-(2,2-dichloroacetamido)-3-fluoro-1-(4-(methylsulfonyl)phenyl)propyl 2-butoxyethyl carbonate The crude product was purified by gel column chromatography to give 93% yield of the title product as a white semi-solid. $H^1$-NMR (DMSO-$d_6$), δ=0.85 ppm (t, 3H), 1.25 ppm (m, 2H), 1.45 ppm (m, 2H), 3.15 ppm (s, 3H), 3.35 ppm (t, 2H), 3.55 ppm (m, 2H), 4.2 ppm (m, 2H), 4.3-4.7 ppm (m, 3H), 5.95 ppm (d, 1H), 6.45 ppm (s, 1H), 7.6 ppm (d, 2H), 7.9 ppm (d, 2H), 9.05 ppm (d, 1H); mass spectrum 524.0 (M+Na).

Example 14

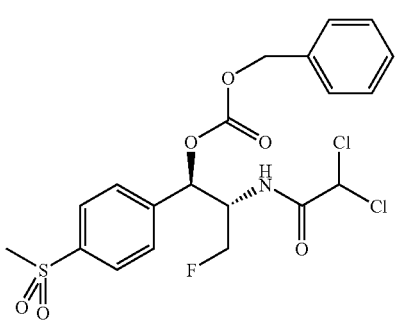

Benzyl(1R,2S)-2-(2,2-dichloroacetamido)-3-fluoro-1-(4-(methylsulfonyl)phenyl)propyl carbonate The crude product was crystallized from isopropanol/ethanol to give 88% yield of the title product as a white solid. $H^1$-NMR (DMSO-$d_6$), δ=3.2 ppm (s, 3H), 4.3-4.7 ppm (m, 3H), 5.15 ppm (s, 2H), 5.9 ppm (d, 1H), 6.4 ppm (s, 1H), 7.38 ppm (s, 5H), 7.6 ppm (d, 2H), 7.9 ppm (d, 2H), 9.05 ppm (d, 1H); mass spectrum 514.0 (M+Na).

Example 16

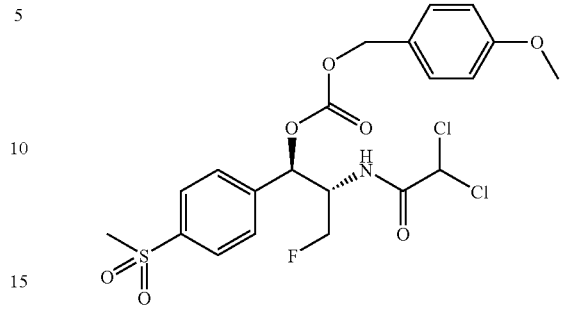

(1R,2S)-2-(2,2-dichloroacetamido)-3-fluoro-1-(4-(methylsulfonyl)phenyl)propyl 4-methoxybenzyl carbonate The crude product was purified by gel column chromatography to give 41% yield of the title product as white semi-solid. $H^1$-NMR (DMSO-$d_6$), δ=3.2 ppm (s, 3H), 3.75 ppm (s, 3H), 4.3-4.7 ppm (m, 3H), 5.05 ppm (s, 2H), 5.9 ppm (d, 1H), 6.4 ppm (s, 1H), 6.9 ppm (d, 2H), 7.25 ppm (d, 2H), 7.6 ppm (d, 2H), 7.9 ppm (d, 2H), 9.05 ppm (d, 1H); mass spectrum 543.9 (M+Na).

Example 15

(1R,2S)-2-(2,2-dichloroacetamido)-3-fluoro-1-(4-(methylsulfonyl)phenyl)propyl 4-methylbenzyl carbonate The crude product was purified by gel column chromatography to give 73% yield of the title product as a white foam. $H^1$-NMR (DMSO-$d_6$), δ=2.3 ppm (s, 3H), 3.2 ppm (s, 3H), 4.3-4.7 ppm (m, 3H), 5.07 ppm (s, 2H), 5.9 ppm (d, 1H), 6.4 ppm (s, 1H), 7.15 ppm (d, 2H), 7.25 ppm (d, 2H), 7.6 ppm (d, 2H), 7.9 ppm (d, 2H), 9.05 ppm (d, 1H); mass spectrum 528.0 (M+Na).

Example 17

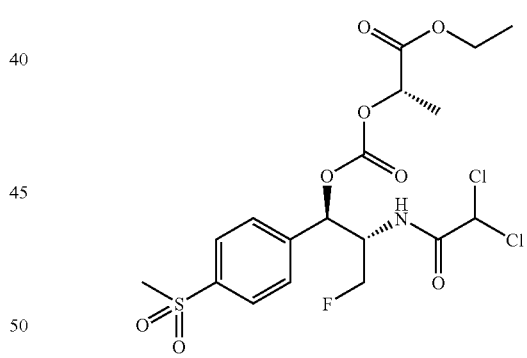

(S)-ethyl 2-(1R,2S)-2-(2,2-dichloroacetamido)-3-fluoro-1-(4-(methylsulfonyl)phenyl)propoxy)carbonyloxy)propanoate The crude product was purified by gel column chromatography to give 71% yield of the title product as a white semi-solid. $H^1$-NMR (DMSO-$d_6$), δ=1.15 ppm (t, 3H), 1.4 ppm (d, 3H), 3.2 ppm (s, 3H), 4.15 ppm (q, 2H), 4.3-4.7 ppm (m, 3H), 4.95 ppm (q, 1H), 5.98 ppm (d, 1H), 6.42 ppm (s, 1H), 7.6 ppm (d, 2H), 7.9 ppm (d, 2H), 9.05 ppm (d, 1H); mass spectrum 523.9 (M+Na).

Example 18

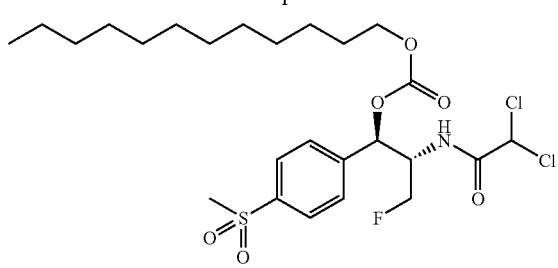

(1R,2S)-2-(2,2-dichloroacetamido)-3-fluoro-1-(4-(methylsulfonyl)phenyl)propyl dodecyl carbonate The crude product was purified by gel column chromatography to give 35% yield of the title product as a white semi-solid. H$^1$-NMR (CDCl$_3$), δ=0.9 ppm (t, 3H), 1.2-1.4 ppm (m, 18H), 1.65-1.75 (m, 2H), 3.1 ppm (s, 3H), 4.1-4.6 ppm (m, 5H), 5.95 ppm (s, 1H), 6.05 ppm (d, 1H), 6.95 ppm (d, 1H), 7.6 ppm (d, 2H), 7.95 ppm (d, 2H).

Example 19

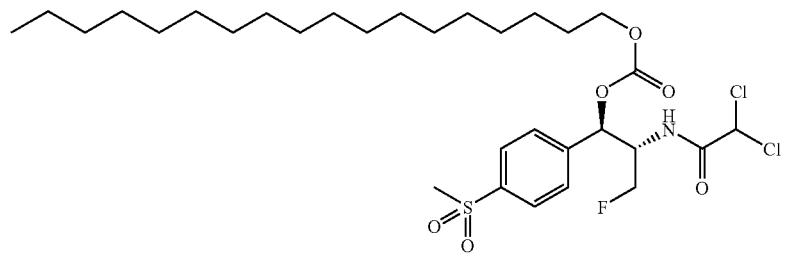

(1R,2S)-2-(2,2-dichloroacetamido)-3-fluoro-1-(4-(methylsulfonyl)phenyl)propyl octadecyl carbonate The crude product was purified by gel column chromatography to give 42% yield of the title product as a white solid. H$^1$-NMR (CDCl$_3$), δ=0.9 ppm (t, 3H), 1.2-1.4 ppm (m, 30H), 1.65-1.75 (m, 2H), 3.05 ppm (s, 3H), 4.1-4.6 ppm (m, 5H), 5.9 ppm (s, 1H), 6.02 ppm (d, 1H), 6.98 ppm (d, 1H), 7.6 ppm (d, 2H), 7.95 ppm (d, 2H).

Example 20

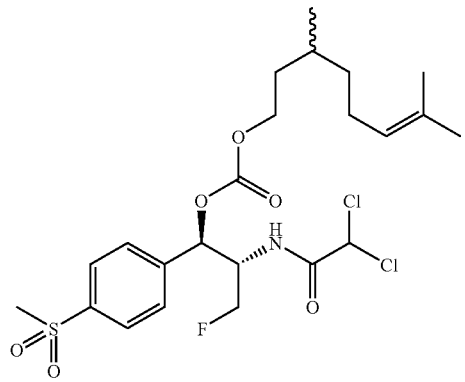

(1R,2S)-2-(2,2-dichloroacetamido)-3-fluoro-1-(4-(methylsulfonyl)phenyl)propyl-(3R,S)-3,7-dimethyloct-6-enyl carbonate The crude product was purified by gel column chromatography to give 30% yield of the title product as a white solid. The structure as drawn illustrates that this is a mixture of isomers. H$^1$-NMR (CDCl$_3$), δ=0.9 ppm (d, 3H), 1.1-2.0 ppm (m, 13H), 3.05 ppm (s, 3H), 4.1-4.6 ppm (m, 5H), 5.05 ppm (t, 1H), 5.9 ppm (s, 1H), 6.0 ppm (d, 1H), 7.0 ppm (d, 1H), 7.6 ppm (d, 2H), 7.95 ppm (d, 2H).

Example 21

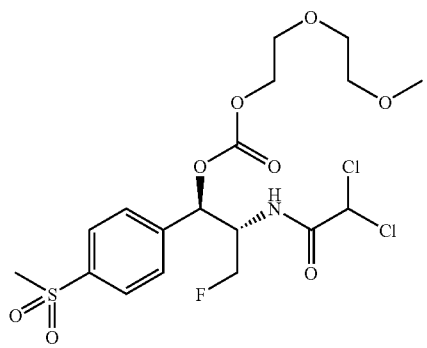

(1R,2S)-2-(2,2-dichloroacetamido)-3-fluoro-1-(4-(methylsulfonyl)phenyl)propyl 2-(2-methoxyethoxy) ethyl carbonate The crude product was purified by gel column chromatography to give the title product as a white solid. H$^1$-NMR (CDCl$_3$), δ=3.05 ppm (s, 3H), 3.38 ppm (s, 3H), 3.55-3.65 ppm (m, 6H), 4.25-4.6 ppm (m, 5H), 5.9 ppm (s, 1H), 6.0 ppm (d, 1H), 7.05 ppm (d, 1H), 7.6 ppm (d, 2H), 7.95 ppm (d, 2H).

Example 22

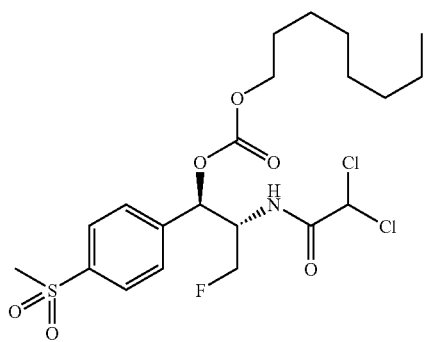

(1R,2S)-2-(2,2-dichloroacetamido)-3-fluoro-1-(4-(methylsulfonyl)phenyl)propyl octyl carbonate The crude product was purified by gel column chromatography to give the desired product to give 44% yield of the title product as a white solid. H$^1$-NMR (CDCl$_3$), δ=0.9 ppm (t, 3H), 1.2-1.4 ppm (m, 12H), 1.65-1.75 (m, 2H), 3.05 ppm (s, 3H), 4.1-4.6 ppm (m, 5H), 5.9 ppm (s, 1H), 6.0 ppm (d, 1H), 6.9 ppm (d, 1H), 7.6 ppm (d, 2H), 7.95 ppm (d, 2H).

Example 23

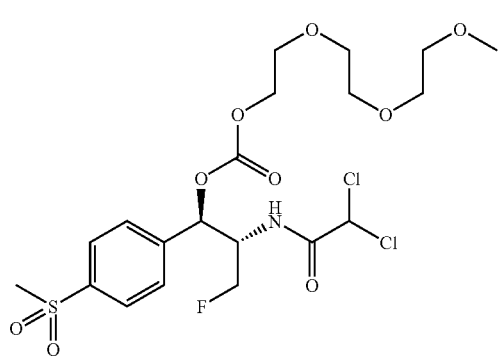

(1R,2S)-2-(2,2-dichloroacetamido)-3-fluoro-1-(4-(methylsulfonyl)phenyl)propyl 2-(2-(2-methoxyethoxy)ethoxy)ethyl carbonate The crude product was purified by gel column chromatography to give 31% yield of the title product as a white semi-solid material. H$^1$-NMR (CDCl$_3$), δ=3.05 ppm (s, 3H), 3.38 ppm (s, 3H), 3.55-3.7 ppm (m, 10H), 4.2-4.6 ppm (m, 5H), 5.95 ppm (m, 2H), 7.25 ppm (d, 1H), 7.6 ppm (d, 2H), 7.95 ppm (d, 2H).

Example 24

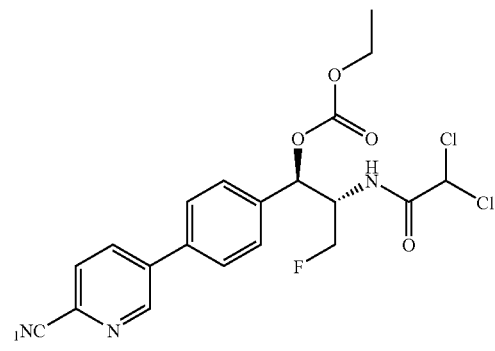

(1R,2S)-1-(4-(6-cyanopyridin-3-yl)phenyl)-2-(2,2-dichloroacetamido)-3-fluoropropyl ethyl carbonate The crude product was purified by gel column chromatography to give 97% yield of the title product as a white foam. H$^1$-NMR (DMSO-d$_6$), δ=1.19 ppm (t, 3H), 4.1 ppm (q, 2H), 4.25-4.6 ppm (m, 3H), 5.05 ppm (s, 2H), 5.9 ppm (d, 1H), 6.2 ppm (t, 1H), 7.5 ppm (d, 2H), 7.85 ppm (d, 2H), 8.1 ppm (d, 1H), 8.35 ppm (d, 1H), 9.1 ppm (s, 1H), 9.3 ppm (d, 1H).

Example 25

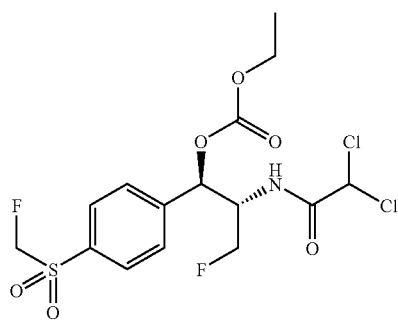

(1R,2S)-2-(2,2-dichloroacetamido)-3-fluoro-1-(4-fluoromethylsulfonyl)phenyl)propyl ethyl carbonate The crude product was purified by gel column chromatography to give quantitative yield of the title product as a white foam. H$^1$-NMR (DMSO-d$_6$), δ=1.2 ppm (t, 3H), 4.1 ppm (q, 2H), 4.3-4.7 ppm (m, 3H), 5.7 ppm (d, 2H), 5.95 ppm (d, 1H), 6.4 ppm (s, 1H), 7.85 ppm (d, 2H), 7.95 ppm (d, 2H), 9.05 ppm (d, 1H).

Example 26

Figure 5:
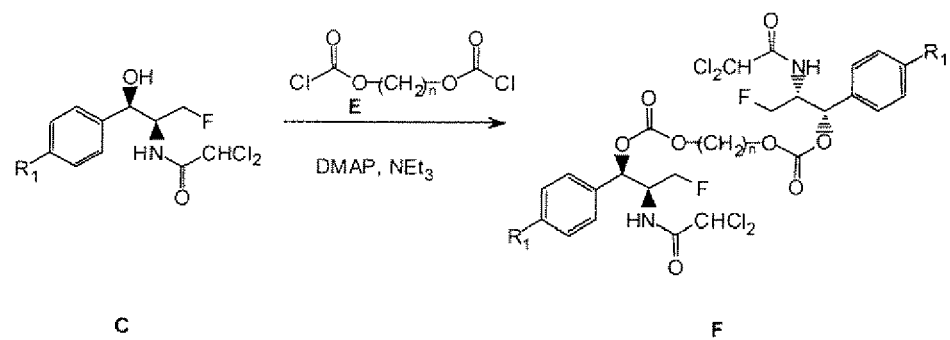
FIG. 5 illustrates the synthesis of bis carbonate fenicol compound F by reacting bis chloroformate E with substrate C to produce carbonate fenicol compound F.

Synthesis of Prodrugs of Florfenicol and its Analogs by Reaction with Bis-Chloroformates of Diols With reference to FIG. 5, an anhydrous tetrahydrofuran solution of the bis chloroformate E (1 molar equivalent, 0.34 M), was placed in a dropping funnel and added dropwise to an anhydrous tetrahydrofuran solution containing substrate C (2.2 molar equivalent, 0.64 M), 4-N,N-dimethylaminopyridine (0.5 molar equivalent), and triethylamine (2.2 molar equivalents) at 0° C. under a nitrogen atmosphere. The mixture was stirred at 0° C. for 30 minutes, and then at room temperature overnight. The resulting solution was rapidly filtered through filter paper to remove the ammonium salt. The filtrate was concentrated and ethyl acetate was added to dissolve the crude product. The resulting solution was washed sequentially with 1 M HCl$_{(aq)}$, saturated NaHCO$_{3(aq)}$, and saturated NaCl$_{(aq)}$, followed by a rapid filtration through a pad of silica gel and Na$_2$SO$_4$. The filtrate was concentrated and the crude product obtained was purified by flash silica gel column chromatography to give the pure carbonate prodrug F.

The following compound was obtained by the above method:

Example 26

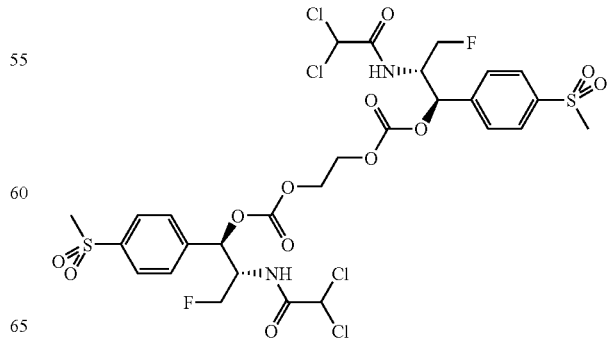

Bis((1R,2S)-2-(2,2-dichloroacetamido)-3-fluoro-1-(4-(methylsulfonyl)phenyl)propyl)ethane-1,2-diyl dicarbonate The crude product was purified by gel column chromatography to give 62% yield of the title product as a white semisolid. H¹-NMR (DMSO-d$_6$), δ=3.2 ppm (s, 6H), 4.3-4.7 ppm (m, 10H), 5.95 ppm (d, 2H), 6.42 ppm (s, 2H), 7.6 ppm (d, 4H), 7.9 ppm (d, 4H), 9.05 ppm (d, 2H); mass spectrum 852.9 (M+Na).

Examples 27-30

Synthesis of Benzylic Carbonate Prodrugs of Chloramphenicol-Type Fenicols (H and I)

Figure 6:
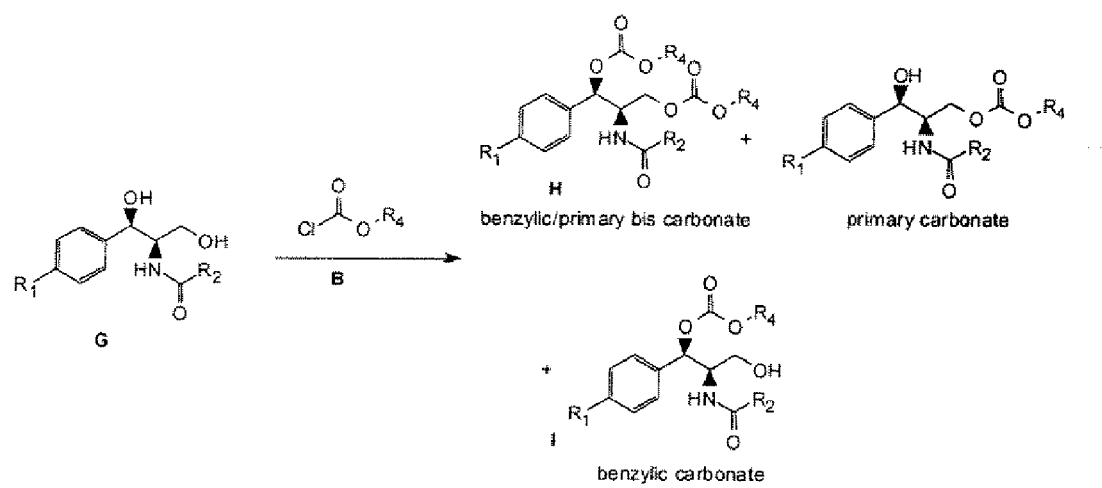
FIG. 6 illustrates the synthesis of carbonate fenicol compound H by reacting ethyl chloroformate B with substrate G, and triethylamine (not shown), to produce benzylic bis carbonate fenicol compound H, benzylic carbonate 1, and a primary carbonate.

The following methods were employed, with reference to FIG. 6.

Method I

An anhydrous tetrahydrofuran solution of ethyl chloroformate B (2.2 molar equivalent, 0.34 M), was placed in a dropping funnel and added drop-wise to an anhydrous tetrahydrofuran solution containing substrate G (1 molar equivalent, 0.64 M), 4-N,N-dimethylaminopyridine (0.5 molar equivalent), and triethylamine (2.4 molar equivalents) at 0° C. under a nitrogen atmosphere. The mixture was stirred at 0° C. for 30 minutes, and then at room temperature overnight. The resulting solution was rapidly filtered through a filter paper to remove the ammonium salt. The filtrate was concentrated and ethyl acetate was added to dissolve the crude product. The resulting solution was washed sequentially with 1 M HCl$_{(aq)}$, saturated NaHCO$_{3(aq)}$, and saturated NaCl$_{(aq)}$, followed by a rapid filtration through a pad of silica gel and Na$_2$SO$_4$. The filtrate was concentrated and the product obtained was dried under reduced pressure to give the pure carbonate prodrug H.

Method II

An anhydrous tetrahydrofuran solution of the ethyl chloroformate B (1 molar equivalent, 0.34 M), was placed in a dropping funnel and added drop-wise to an anhydrous tetrahydrofuran solution containing substrate G (1 molar equivalent, 0.64 M), 4-N,N-dimethylaminopyridine (0.5 molar equivalent), and triethylamine (2.4 molar equivalents) at 0° C. under a nitrogen atmosphere. The mixture was stirred at 0° C. for 30 minutes, and then at room temperature overnight. The resulting solution was rapidly filtered through a filter paper to remove the ammonium salt. The filtrate was concentrated and ethyl acetate was added to dissolve the crude product. The resulting solution was washed sequentially with 1 M HCl$_{(aq)}$, saturated NaHCO$_{3(aq)}$, and saturated NaCl$_{(aq)}$, followed by a rapid filtration through a pad of silica gel and Na$_2$SO$_4$. The filtrate was concentrated and the crude product obtained was purified by flash silica gel column chromatography to give the pure carbonate prodrugs H and I.

The following example compounds were obtained by the above method:

| Example No. | Compound Name |
| --- | --- |
| 27 | (1R,2S)-2-(2,2-dichloroacetamido)-1-(4-nitrophenyl)propane-1,3-diyldiethyl dicarbonate. |
| 28 | (1R,2R)-2-(2,2-dichloroacetamido)-3-hydroxy-1-(4-nitrophenyl)propyl ethyl carbonate. |
| 29 | (1R,2R)-2-(2,2-dichloroacetamido)-1-(4-(methylsulfonyl)phenyl)propane-1,3-diyl diethyl dicarbonate. |
| 30 | (1R,2R)-2-(2,2-dichloroacetamido)-3-hydroxy-1-(4-(methylsulfonyl)phenyl)propyl ethyl carbonate. |

Example 27

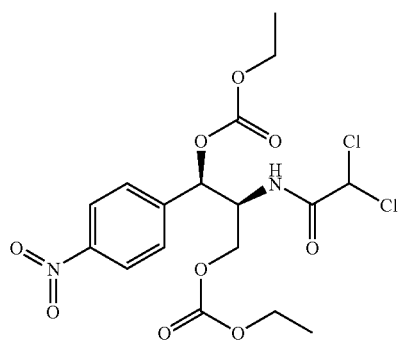

(1R,2S)-2-(2,2-dichloroacetamido)-1-(4-nitrophenyl) propane-1,3-diyl diethyl dicarbonate The product was obtained by Method I, supra, to give 88% yield of the title product as a white foam. This product was also obtained by Method II to give 25% yield of the title product as a white foam. H¹-NMR (DMSO-d$_6$), δ=1.2 ppm (m, 6H), 4.05-4.25 ppm (m, 6H), 4.5 ppm (m, 1H), 5.95 ppm (d, 1H), 6.4 ppm (s, 1H), 7.6 ppm (d, 2H), 8.2 ppm (d, 2H), 8.95 ppm (d, 1H).

Example 28

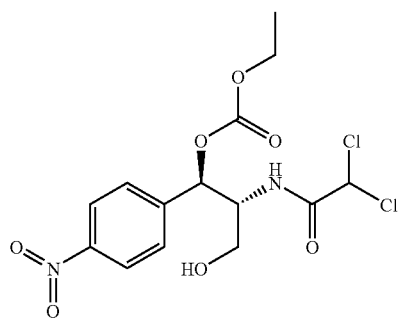

(1R,2R)-2-(2,2-dichloroacetamido)-3-hydroxy-1-(4-nitrophenyl)propyl ethyl carbonate The product was obtained by Method II, supra, to give 19% yield of the title product as a white foam. H¹-NMR (DMSO-d$_6$), δ=1.2 ppm (t, 3H), 3.35 ppm (m, 1H), 3.45 ppm (m, 1H), 4.0-4.2 ppm (m, 3H), 5.19 ppm (t, 1H), 5.9 ppm (d, 1H), 6.4 ppm (s, 1H), 7.6 ppm (d, 2H), 8.2 ppm (d, 2H), 8.75 ppm (d, 1H).

Example 29

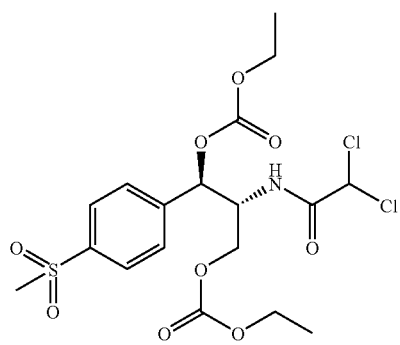

(1R,2R)-2-(2,2-dichloroacetamido)-1-(4-(methylsulfonyl)phenyl)propane-1,3-diyl diethyl dicarbonate The crude product was obtained by Method II, supra, to give 19% yield of the title product as a white foam. $H^1$-NMR (DMSO-$d_6$), δ=1.2 ppm (m, 6H), 3.19 ppm (s, 3H), 4.05-4.25 ppm (m, 6H), 4.45 ppm (m, 1H), 5.9 ppm (d, 1H), 6.4 ppm (s, 1H), 7.6 ppm (d, 2H), 7.9 ppm (d, 2H), 8.95 ppm (d, 1H).

Example 30

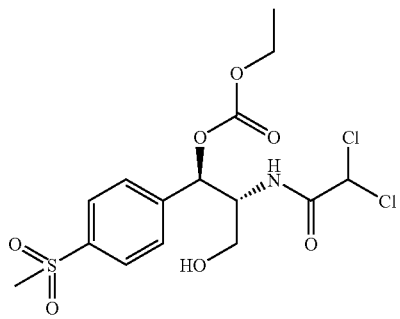

(1R,2R)-2-(2,2-dichloroacetamido)-3-hydroxy-1-(4-(methylsulfonyl)phenyl)propyl ethyl carbonate The crude product was obtained by Method II, supra, to give 20% yield of the title product as a white foam. $H^1$-NMR (DMSO-$d_6$), δ=1.2 ppm (t, 3H), 3.2 ppm (s, 3H), 3.35 ppm (m, 1H), 3.45 ppm (m, 1H), 4.0-4.2 ppm (m, 3H), 5.19 ppm (t, 1H), 5.85 ppm (d, 1H), 6.42 ppm (s, 1H), 7.58 ppm (d, 2H), 7.9 ppm (d, 2H), 8.75 ppm (d, 1H).

Examples 31-35

Evaluation of the Utility of Florfenicol Benzylic Carbonate Prodrugs

Example 31

Viscosity of Compositions

Table 4, below, provides evaluations of the syringeability of dosing solutions of selected florfenicol benzylic carbonate prodrugs at concentrations equivalent to 300 mg/ml florfenicol (30% weight/volume).

TABLE 4

| | Prodrug of Example | Concentration (mg/ml) | Solvent mixture (vol/vol composition) | Syringeability measurement[c] Dripping time (sec) | Relative to NUFLOR ® |
|---|---|---|---|---|---|
| 1 | 2 | 358 | Triacetin/benzyl alcohol - 2:1 | 128 ± 7 | 0.55 |
| 2 | 2 | 418[a] | Triacetin/benzyl alcohol - 2:1 | 207 ± 3 | 0.89 |
| 3 | 2 | 358 | Triacetin/benzyl alcohol - 2:1.5 | 97 ± 1 | 0.42 |
| 4 | 2 | 358 | 2-pyrolidinone/benzyl alcohol - 1:1 | 108 ± 1 | 0.46 |
| 5 | 2 | 358 | Triacetin/2-pyrolidinone - 1:1 | 268 ± 4 | 1.15 |
| 6 | 4 | 372 | Triacetin/benzyl alcohol/2-pyrolidinone - 2:1:1.5 | 164 ± 3 | 0.70 |
| 7 | 8 | 396 | Triacetin/benzyl alcohol/2-pyrolidinone - 2:1:1.5 | 157 ± 1 | 0.67 |
| 8 | 13 | 421 | Triacetin/benzyl alcohol - 2:1 | 141 ± 5 | 0.61 |
| 9 | 14 | 412 | Triacetin/benzyl alcohol - 2:1 | 204 ± 9 | 0.88 |
| 10 | 26 | 348 | Triacetin/benzyl alcohol - 2:1 | 216 ± 8 | 0.93 |
| 11 | 4 + Florfenicol | 248 + 100 | Triacetin/benzyl alcohol/2-pyrolidinone - 4:2:1 | 164 ± 3 | 0.70 |
| 12 | 14 + Florfenicol | 275 + 100 | Triacetin/benzyl alcohol - 2:1 | 168 ± 2 | 0.72 |
| 13 | Florfenicol | 300 | [b]N-methyl 2-pyrolidinone/propylene glycol/polyethylene glycol 300 | 233 ± 2 | 1.00 |

[a]Concentration of benzylic carbonate prodrug corresponding to 35% weight by volume concentration of florfenicol.
[b]solution prepared by using for each milliliter of solution 300 mg of florfenicol, 250 mg N-methyl-2-pyrolidinone, 150 mg propylene glycol and polyethylene glycol 300 q.s.
[c]as evaluated by dripping-syringe method described below.

Discussion

High concentrations of fenicol or fenicol drug contained in a fenicol prodrug are often necessary for convenient administration of the necessary amount of the desired amount of the antibiotic. Due to the limited solubility of fenicols in many organic solvents or mixtures of solvents acceptable for injectable formulations the choice of solvents for preparation of highly concentrated florfenicol solutions is limited. As a result highly concentrated solutions of fenicol drugs in organic solvents or solvent mixtures may become highly viscous and difficult to administer by a syringe. Therefore the ability of fenicol benzylic carbonate prodrugs to dissolve in a wider range of organic solvents or mixtures of solvents acceptable for injectable formulations offered the potential to prepare highly concentrated solutions for injections with lower viscosity. Table 4 shows comparisons of syringeabilities of concentrated solutions of florfenicol benzylic carbonate prodrugs in examples of mixtures of organic solvents which are generally acceptable for injectable subcutaneous or intramuscular dosing. Test solutions of florfenicol benzylic carbonates containing concentrations of florfenicol (mg/mL) equivalent to the concentration present in Nuflor® formulation were prepared. Syringeabilities of the solutions were evaluated by means of the "dripping syringe" method in which the dripping times (sec) of equal volumes of such solutions under free gravitational flow conditions from a vertically positioned syringe were measured at 15° C. After removing the plunger from a 5 ml polyethylene disposable syringe (5 ml Luer, Norm-Ject Zentrish/Henke Saas Wolf GMBH) and fitting the syringe with a disposable needle (B-D® 16G1 Precision Glide/BentonDickinson & CO) the test solutions were loaded from the top into the syringe and the time necessary for the free flow of 2 mL of solution (between 3 ml and 1 ml marks) was recorded in triplicate. The syringeabilities relative to Nuflor® were calculated by dividing the dripping time for the test solutions (entries 1-12) by the dripping time measured for the commercial sample of Nuflor® formulation (entry 13) As it is evident from the results in Table 4 the syringeabilities of tested solutions containing benzyl alcohol as viscosity diluent had relative syringeabilities <1.00 and were therefore better than Nuflor® (30% weight/volume florfenicol solution in propylene glycol/polyethylene glycol 300/2-methyl pyrolidinone). Due to their better syringeability these solutions represent more favorable formulations for injectable delivery of florfenicol. Solution of the florfenicol benzylic carbonate of the example 2 in triacetin/2-pyrolidinone—1/1 lacking the benzyl alcohol viscosity diluent was the only solution with syringeability poorer that than that of Nuflor® (entry 5). Solution of the florfenicol benzylic carbonate of the example 2 containing higher concentration of florfenicol than Nuflor® (entry 2; 35% w/v vs. 30% w/v) also displayed superior syringeability. Interestingly solutions containing concentrations of florfenicol equivalent to 30% w/v in mixed form of free florfenicol and florfenicol benzylic carbonate prodrug (entries 11-12) also displayed syringeability superior to Nuflor® formulation.

Example 32

Melting Point and Aqueous Solubility Comparisons

Modifications of physicochemical properties achievable with carbonate prodrugs of fenicols, or benzylic carbonate prodrugs of fenicols (analogs of fenicol) are important for the ability to obtain the desired organic solvent based formulations for animal administration. Higher solubilities of fenicol benzylic carbonate prodrugs as compared to parent fenicols in certain organic solvents or mixtures of organic solvents are due in part to the lower melting points of such carbonate prodrugs as compared to parent drugs. These lower melting points reflect the reduced energy of the crystal lattice of the carbonate prodrugs which is responsible for the increased solubility. Comparison of the melting points of florfenicol of the available crystal forms of various examples of florfenicol prodrugs are shown in Table 5, below.

In some therapeutic applications florfenicol is administered in concentrated organic solution subcutaneously where it is known to form localized depot of the drug which results in the desired sustained release of the drug into the circulation. In such cases solubility of florfenicol in aqueous media represents one of important factors determining the rate of the sustained release. Another important factor affecting the sustained release of florfenicol from the subcutaneous depot site is the concentration of the dosing solution and the solvent composition of the formulation. Apart from the broader range of solvents which can be used for acceptable formulations of florfenicol benzylic carbonate prodrugs these prodrugs also allow a wide range of aqueous solubilities. Aqueous solubilities which were measured for a number of florfenicol benzylic carbonate prodrugs are shown in Table 5. Solubilities achieved with these prodrugs range from slightly to dramatically lower than that of florfenicol. Reduced aqueous solubilities of such prodrugs may be useful in controlling the rate of dissolution of the prodrug at the subcutaneous depot site and may allow achieving optimized sustained release of the parent drug.

TABLE 5

Physicochemical properties of selected benzylic carbonate prodrugs of florfenicol: melting points and aqueous solubilities of selected examples.

| Prodrug of Example | Melting point (crystallization solvent) | Aqueous solubility |
|---|---|---|
| 2 | 110-112° C. (isopropanol) | 0.69 mg/ml |
| 4 | 148-150° C. (isopropanol) | 0.10 mg/ml |
| 5 | 156-158° C. (isopropanol/ethanol) | 0.007 mg/ml |
| 6 | 132-134° C. (ethyl acetate/hexane) | 0.12 mg/ml |
| 8 | 120-122° C. (ethyl acetate/hexane) | 0.025 mg/ml |
| 11 | oil (—)$^a$ | 0.77 mg/ml |
| 12 | 88-90° C. (—)$^a$ | 0.35 mg/ml |
| 13 | oil (—)$^a$ | 0.15 mg/ml |
| 14 | 105-106° C. (isopropanol) | 0.032 mg/ml |
| 17 | 44-54° C. (—)$^a$ | 0.55 mg/ml |
| 26 | 110-112° C. (—)$^a$ | 0.045 mg/ml |
| Florfenicol | 153-154° C. | 1.53 mg/ml |

$^a$— not crystallized; melting point was measured if the solid material was obtained after evaporation of the solvent from the column chromatography fractions.

Example 33

Comparisons of Solubilities in Organic Solvents (Triacetin/Benzyl Alcohol 2:1 Mixture Table 6, below, illustrates the solubilities of florfenicol equivalents which were achieved with selected benzylic carbonate florfenicol prodrugs in an example solvent mixture triacetin/benzyl alcohol 2:1 (volume/volume) employing benzyl alcohol as the low viscosity component. Desired concentrations of equal or greater than 30% (weight/volume) were achieved with the benzylic carbonate florfenicol prodrugs. Florfenicol parent drug was not soluble in triacetin/benzyl alcohol 2:1 (volume/volume) even at concentrations as low as 10% (weight/volume). Interestingly florfenicol became more soluble in triacetin/benzyl alcohol 2:1 (volume/volume) when benzylic carbonate prodrug of florfenicol was also present. The combination of prodrug of Example 14 at 275 mg/ml and florfenicol at 100 mg/ml was soluble in triacetin/benzyl alcohol 2:1 (volume/volume) and provided a stable solution with 30% (weight/volume) content of florfenicol (Table 4, supra, entry 12).

TABLE 6

Solubility at selected concentrations of contained florfenicol (% weight/volume) 20° C. in form of benzylic carbonate prodrugs, prodrugs in triacetin/benzyl alcohol 2:1 (volume/volume) solvent mixture.

| Prodrug of Example | 10% | 20% | 25% | 30% | 35% | 37% | 40% |
|---|---|---|---|---|---|---|---|
| 2 | soluble | soluble | soluble | soluble | soluble | soluble | insoluble |
| 13 | soluble | soluble | soluble | soluble | soluble | soluble | soluble |
| 14 | soluble | soluble | soluble | soluble | soluble | soluble | insoluble |
| 26 | soluble | soluble | soluble | soluble | soluble | soluble | soluble |
| florfenicol | insoluble | insoluble | insoluble | insoluble | insoluble | insoluble | insoluble |

Example 34

In Vitro Enzymatic Release of Parent Florfenicol from Benzylic Carbonate Prodrugs The ability of a prodrug derivative of a parent drug molecule to act efficiently in vivo as a source of the free parent drug determines the utility of a particular prodrug for treatment. The prodrug's ability to release the parent drug in vivo, in the presence of endogenous enzymes, can be determined by measuring the systemic levels of the parent drug after administration of the prodrug to the animal. This releasibility can also be assessed in vitro by measuring the release of the parent drug after mixing with animal whole blood, plasma or serum. Selected benzylic carbonate prodrugs of florfenicol were tested for release of florfenicol after in vitro mixing with bovine serum. The tested compounds displayed favorable parent drug release profiles as shown in Table 7, below. The compounds of Examples 8 and 14 displayed the highest rates of rates of florfenicol release in serum. A general trend of more lipophilic carbonates of florfenicol showing higher rates of degradation and release seems to be present among the compounds tested. An interesting exception was found to be represented by Example 26 (bis-florfenicol carbonate).

TABLE 7

| Prodrug of Example | Florfenicol released from prodrugs (% of total) at different time-points after treatment with bovine serum. | | | | |
|---|---|---|---|---|---|
| | 0 | 1 h | 2 h | 4 h | 8 h | 24 h |
| 2 | BQL[a] | BQL | BQL | 4.5 | 12.6 | 23.3 |
| 4 | BQL | BQL | BQL | 4.8 | 6.6 | 21.4 |
| 8 | BQL | 36.9 | 54.9 | 81.5 | 84.0 | 96.3 |
| 13 | BQL | BQL | 8.5 | 13.6 | 22.6 | 40.0 |
| 14 | BQL | 28.9 | 42.3 | 79.5 | 81.4 | 94.1 |
| 26 | BQL | BQL | 18.2 | 32.7 | 44.9 | 69.4 |

[a]BQL—below quantification limit 50 microliter of stock solution of carbonate pro-drug (10 mg/mL in DMSO) was added to 5 mL donor bovine serum and mixed. Aliquots of 400 microliter of the resulting solution were transferred into 1.5 mL plastic centrifuge tubes. Each plastic tube was placed into at 37° C. water bath for incubation. Samples were removed at 0, 1, 2, 4, 8, and 24 hours, and after addition of 400 microliter of acetonitrile to stop the reaction, rapidly stirred for 30 seconds. The precipitate was removed by centrifugation on an Eppendorf 5415G at 14000 rpm for 5 minutes. The clear supernatant solution was sampled for the HPLC analysis. The peak area of florfenicol was used to calculate the conversion of the prodrugs.
HPLC conditions were as follows:

| HPLC conditions were as follows: | |
|---|---|
| System: | Agilent 1100 series |
| Column: | Varian Microsorb - 5µ, C18, 150 mm × 2.1 mm |
| Column Temp: | 30° C. |
| Flow rate: | 0.5 mL/min |
| Injection Volume: | 40 µl |
| Organic: | Acetonitrile |
| Aqueous: | 0.1% formic acid in water |
| Run Time: | 20 min |

| Gradient was as follows: | |
|---|---|
| Time (min), | % Organic |
| 0 | 5 |
| 15 | 40 |
| 17 | 40 |
| 18 | 5 |

The results of testing the stability of selected prodrugs in bovine serum presented in Table 7 confirmed that benzylic carbonates of florfenicol release the parent drug when treated in vitro with serum enzymes. These results provide evidence that benzylic carbonates of florfenicol are substrates of hydrolytic enzymes present in bovine serum.

Example 35

In Vivo Release of Parent Florfenicol from Benzylic Carbonate Prodrugs

The pharmacokinetic profile of active antibiotic after prodrug administration, in vivo, was determined, as follows:
1. In vivo release of active antibiotic confirmed in two different animal species:
    The prodrug compound of Example 18 was administered by an intravenous ("IV") route to rat and cattle subjects, followed by determination of florfenicol concentrations in the plasma collected over time.
    The data of Table 8, below, illustrates the plasma levels of florfenicol that resulted following IV administration of the prodrug compound of Example 18, to both rat and cattle.

TABLE 8

| Compound of Ex. No. | Species | Dose (mg/kg) | Route | AUC (hr · mg/L) | Cmax (mg/L) |
|---|---|---|---|---|---|
| 18 | Rat (n = 3) | 20 | IV | 26.4 ± 16.8 | 6.2 ± 3.8 |
| 18 | Cattle (n = 3) | 10 | IV | 20.2 ± 2.8 | 0.6 ± 0.1 |

2. Active antibiotic is released from the prodrug irrespective of route of administration of the prodrug:

The data of Table 9, below, illustrates the plasma levels of florfenicol that resulted following administration of the prodrug compound of Example 2, by two different routes, i.e., IV and subcutaneous ("SC").

TABLE 9

| Compound of Ex. No. | Species | Dose (mg/kg) | Route | AUC (hr · mg/L) | Cmax (mg/L) |
|---|---|---|---|---|---|
| 2 | Cattle (n = 3) | 9 | IV | 18 ± 1.7 | 3.6 ± 0.8 |
| 2 | Cattle (n = 3) | 18 | SC | 42.6 ± 13.7 | 1.6 ± 0.8 |

3. A dose-dependant increase in the release of active moiety:

The data of table 10, below, confirms a dose-dependent increase in the plasma levels of active antibiotic (florfenicol) following administration of rising doses of prodrug compound of Example 2.

TABLE 10

| Compound of Ex. No. | Species | Dose (mg/kg) | Route | AUC (hr · mg/L) | Cmax (mg/L) |
|---|---|---|---|---|---|
| 2 | Cattle (n = 3) | 18 | SC | 42.6 ± 13.7 | 1.6 ± 0.8 |
| 2 | Cattle (n = 5) | 42 | SC | 152.6 ± 77 | 2.7 ± 1.3 |

4. Time of release of active moiety:

a. The data of Tables 11 and 12, below, confirm that the active antibiotic (florfenicol) is released in less than half an hour after administration of the prodrug compound of Example 2, irrespective of the species.

TABLE 11

20 mg/kg in Rats by IV Route

| Time (hr) | Florfenicol (mg/L) Mean ± SD* |
|---|---|
| 0.08 | 9.1 ± 1.5 |
| 0.25 | 16.6 ± 0.1 |
| 0.50 | 10.2 ± 1.1 |
| 0.75 | 9.4 ± 0.6 |
| 1 | 7.0 ± 0.3 |
| 1.5 | 5.2 ± 0.1 |
| 2 | 4.0 ± 0.3 |
| 4 | 1.2 ± 0.2 |
| 6 | 0.5 ± 0.02 |

*Measured in plasma

TABLE 12

9 mg/kg in Cattle by IV Route

| Time (hr) | Florfenicol (mg/L) Mean ± SD* |
|---|---|
| 0.50 | 2.37 ± 2.11 |
| 1.00 | 7.32 ± 8.05 |
| 2.00 | 1.78 ± 1.22 |
| 4.00 | 1.39 ± 0.56 |
| 10.00 | 0.38 ± 0.22 |
| 24.00 | 0.14 ± 0.14 |

*Measured in plasma b. The data of tables 13 and 14, below, confirms that the active antibiotic is quickly released from the prodrug compound of Example 2, when administered by the IV and SC routes in cattle.

TABLE 13

48 mg/kg in Cattle by SC Route

| Time (hr) | Florfenicol (mg/L) Mean ± SD* |
|---|---|
| 0.5 | 1.01 ± 1.24 |
| 1 | 1.56 ± 1.68 |
| 2 | 2.00 ± 1.55 |
| 4 | 2.19 ± 0.73 |
| 7 | 2.16 ± 0.28 |
| 24 | 1.36 ± 0.2 |
| 31 | 1.01 ± 0.07 |
| 48 | 0.58 ± 0.1 |
| 55 | 0.51 ± 0.07 |
| 72 | 0.38 ± 0.11 |
| 79 | 0.34 ± 0.11 |
| 144 | 0.15 ± 0.08 |

*Measured in plasma

TABLE 14

9 mg/kg in Cattle by IV Route

| Time (hr) | Florfenicol (mg/L) Mean ± SD* |
|---|---|
| 0.50 | 2.37 ± 2.11 |
| 1.00 | 7.32 ± 8.05 |
| 2.00 | 1.78 ± 1.22 |
| 4.00 | 1.39 ± 0.56 |
| 10.00 | 0.38 ± 0.22 |
| 24.00 | 0.14 ± 0.14 |

*Measured in plasma

5. Effect of formulation:

Advantages of triacetin/benzyl alcohol formulation of the fenicol carbonate prodrug.

The release kinetics of the compound of Example 2 were compared with administration in a formulation with a triacetin/benzyl alcohol (ratio of 2:1 wt/vol) and with administration in a formulation of triacetin/2-pyrrolidinone (ratio of 2:1 wt/vol). The study was conducted in cattle (n=3).

Mean AUC values after SC administration of the compound of Example 2, administered in a dose of 20 mg/kg in triacetin/2-pyrrolidinone were 42.6 hr·mg/L.

Mean AUC values after SC administration of the compound of Example 2, administered in a dose of 40 mg/kg in triacetin/benzyl alcohol were 152.1 hr·mg/L.

Because the dose used in the two studies differed, the dose-normalized values were calculated, and were 2.13 hr/L (42.6/20) and 3.8 hr/L (152.1/40) for triacetin/2-pyrrolidinone and triacetin/benzyl alcohol, respectively.

6. Bioavailability of florfenicol in cattle after subcutaneous administration of benzylic carbonate prodrug of Example 2.

Calculation of pharmacokinetic data for the compound of Example 2:
Total Average active moiety (Florfenicol) AUC=152.11 hr·mg/L
Total Average AUC of the compound of Example 2=38.04, which in turn is equal to 30.43 hr·mg/L Florfenicol Equivalent.
83.5% of MC-9148 was converted to Florfenicol once absorbed from SC site.

Efficacy Studies with the Compound of Example 2

Therapeutic efficacy of a single dose of Nuflor® (Schering-Plough Animal Health) was compared with a single dose of the prodrug compound of Example 2 after SC administration in cattle suffering from naturally occurring bovine respiratory disease (BRD). The results are as follows:

TABLE 15

| Group | # of animals | Dose | Route | Temp. °C. (day 0) | Temp. °C. (day 3) | Temp. °C. (day 10) | Treatment Failure (on day 10) |
|---|---|---|---|---|---|---|---|
| Saline | 12 | 0.1 ml/kg | S/C | 40.7 | 40.2 | Discont.*** | 12 out of 12 |
| Nuflor ®* | 24 | 40 mg/kg | S/C | 40.6 | 38.6 | 38.6 | 4 out of 24 |
| Cpnd of Example 2 | 24 | 48 mg/kg** | S/C | 40.4 | 38.8 | 38.7 | 5 out of 24 |

*300 mg/ml of florfenicol
**Equivalent to 40 mg/kg of florfenicol
***Saline-treated animals were discontinued on day 3 because of lack of improvement in the disease symptoms.

In conclusion, the efficacy observed with florfenicol, which was released from the prodrug of Example 2, is comparable to the marketed brand of florfenicol (Nuflor®).

Conclusion

Thus, it will be appreciated that the present invention provides novel prodrugs of fenicol antibiotics and methods for their use in the treatment or prevention of bacterial infection in animals or humans.

Although certain embodiments and examples have been used to describe the present invention, it will be apparent to those skilled in the art that changes in the embodiments and examples shown may be made without departing from the scope of this invention.

What is claimed is:

1. A fenicol carbonate of Formula I, or a solvate thereof,

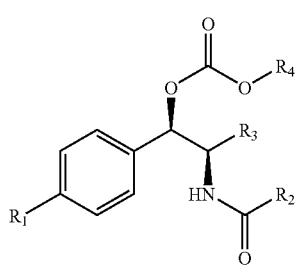

Formula I wherein $R_1$ is selected from the group consisting of

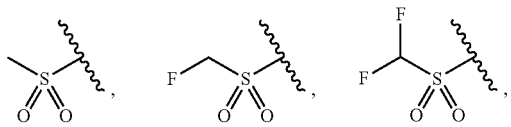

$R_2$ is selected from a group consisting of dichloromethyl, difluoromethyl, chlorfluoromethyl, chloromethyl and methyl, $R_3$ is selected from a group consisting of hydroxymethyl, fluoromethyl, difluoromethyl, trifluoromethyl and $CH_2O$—$C(O)O$—$R_5$, $R_4$ and $R_5$ are independently selected from the group consisting of substituted or unsubstituted $C_{1-10}$ straight, branched or cyclo alkyl, substituted or unsubstituted $C_{1-10}$ alkoxyalkyl, $C_{1-10}$ aryl, $C_{1-10}$ arylalkyl, substituted or unsubstituted $C_{1-10}$ straight, branched or cycloalkenyl.

2. The fenicol carbonate of claim 1 wherein $R_4$ and $R_5$ are independently selected from the group consisting of methyl, ethyl, propyl, isopropyl, n-butyl, tert-butyl, isobutyl, pentyl, isopentyl, n-hexyl, n-heptyl, n-octyl, n-nonyl, n-decyl, n-dodecyl, n-octadecyl, 2-methyl-butyl, 1-ethyl-propyl, 3-methyl-prop-2-enyl, 2-methoxy-ethyl, 2-ethoxy-ethyl, 2-propoxy-ethyl, 2-butoxy-ethyl, 1-methyl-2-methoxy-ethyl, cyclopropyl-methyl, cyclopentyl-methyl, cyclohexyl-methyl, cyclopropyl, cyclobutyl, cyclopentyl, cyclohexyl, 3,7-dimethyloct-6-enyl, benzyl, 2-methyl-benzyl, 3-methyl-benzyl, 4-methyl-benzyl, 2-methoxy-benzyl, 3-methoxy-benzyl, 4-methoxy-benzyl, methyl-2-furyl, 2-(methoxy-ethoxy)-ethyl, 2-(ethoxy-ethoxy)-ethyl, 2-[2-(methoxy-ethoxy)-ethoxy]-ethyl, 2-[2-(ethoxy-ethoxy)-ethoxy]-ethyl, 2-(hydroxy-ethoxy)-ethyl, 2-[2-(hydroxy-ethoxy)-ethoxy]-ethyl, 2-acetoxy-ethyl, 2-(acetoxy-ethoxy)-ethyl, 3-acetoxy-propyl, 2-carboxy-ethyl, 3-carboxy-propyl, 4-carboxy-butyl, 2-methoxycarbonyl-ethyl, 3-methoxycarbonyl-propyl, 4-methoxycarbonyl-butyl, 2-methoxycarbonyl-benzyl, 3-methoxycarbonyl-benzyl, 4-methoxycarbonyl-benzyl, 1-ethoxycarbonyl-ethyl, 1-methoxycarbonyl-ethyl, phenyl, 4-methyl-phenyl, 4-methoxy-phenyl, 4-carboxy-phenyl, 2-carboxy-phenyl, 4-methoxycarbonyl-phenyl, 2-methoxycarbonyl-phenyl and 4-acetylamino-phenyl.

3. The fenicol carbonate of claim 2 wherein $R_4$ and $R_5$ are independently substituted with a moiety selected from the group consisting of methyl, methoxy, carboxy, carboalkoxy and acyloxy.

4. The fenicol carbonate of claim 2, wherein $R_1$ is selected from the group consisting of

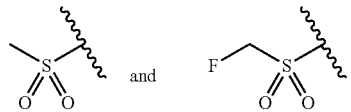

and $R_2$ is dichloromethyl or difluoromethyl, and $R_3$ is selected from the group consisting of hydroxymethyl, fluoromethyl and $CH_2O—C(O)O—R_5$.

5. The fenicol carbonate of claim 1 wherein $R_1$ is $CH_3SO_2$, $R_2$ is $CHCl_2$ and $R_3$ is $CH_2F$.

6. The florfenicol carbonate of claim 5, wherein $R_4$ is selected from the group consisting of methyl, ethyl, propyl, isopropyl, n-butyl, tert-butyl, isobutyl, pentyl, isopentyl, n-hexyl, n-heptyl, n-octyl, n-nonyl, n-decyl, n-dodecyl, n-octadecyl, 2-methyl-butyl, 1-ethyl-propyl, 3-methyl-prop-2-enyl, 2-methoxy-ethyl, 2-ethoxy-ethyl,2-propoxy-ethyl, 2-butoxy-ethyl, 1-methyl-2-methoxy-ethyl, cyclopropyl-methyl, cyclopentyl-methyl, cyclohexyl-methyl, cyclopropyl, cyclobutyl, cyclopentyl, cyclohexyl, 3,7-dimethyloct-6-enyl, benzyl, 2-methyl-benzyl, 3-methyl-benzyl, 4-methyl-benzyl, 2-methoxy-benzyl, 3-methoxy-benzyl, 4-methoxy-benzyl, methyl-2-furyl, 2-(methoxy-ethoxy)-ethyl, 2-(ethoxy-ethoxy)-ethyl,2-[2-(methoxy-ethoxy)-ethoxy]-ethyl, 2-[2-(ethoxy-ethoxy)-ethoxy]-ethyl, 2-(hydroxy-ethoxy) -ethyl, 2-[2-(hydroxy-ethoxy)-ethoxy]-ethyl, 2-acetoxy-ethyl, 2-(acetoxy-ethoxy) -ethyl, 3-acetoxy-propyl, 2-carboxy-ethyl, 3-carboxy-propyl, 4-carboxy-butyl, 2-methoxycarbonyl-ethyl, 3-methoxycarbonyl-propyl, 4-methoxycarbonyl-butyl, 2-methoxycarbonyl-benzyl, 3-methoxycarbonyl-benzyl, 4-methoxycarbonyl-benzyl, 1-ethoxycarbonyl -ethyl, 1-methoxycarbonyl-ethyl, phenyl, 4-methyl-phenyl, 4-methoxy-phenyl, 4-carboxy-phenyl, 2-carboxy-phenyl, 4-methoxycarbonyl-phenyl, 2-methoxycarbonyl-phenyl and 4-acetylamino-phenyl.

7. The fenicol carbonate of claim 1, wherein $R_3$ is $CH_2F$.

8. The fenicol carbonate of claim 1, wherein $R_1$ is $CH_3SO_2$ $R_2$ is $CHCl_2$, $R_3$ is OH and $R_4$ is ethyl.

9. The fenicol carbonate of claim 1, wherein $R_1$ is $CH_3SO_2$, $R_2$ is $CHCl_2$, $R_3$ is

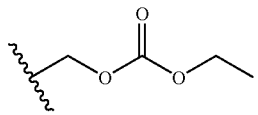

and $R_4$ is ethyl.

10. The fenicol carbonate of claim 1 that is selected from the group consisting of

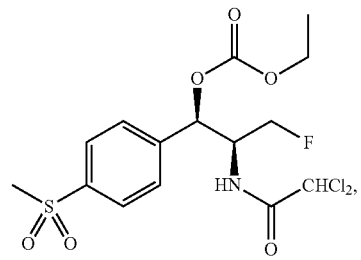

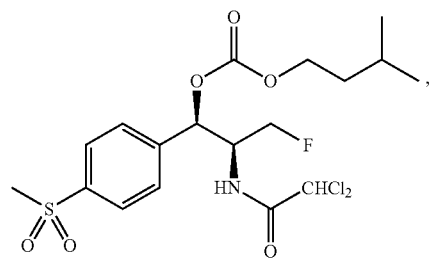

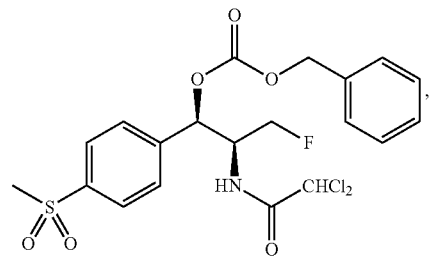

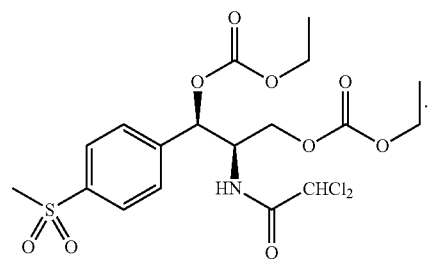

11. The fenicol carbonate of claim 1 that is selected from the group consisting of the following compounds
(1R,2S)-2-(2,2-dichloroacetamido)-3-fluoro-1-(4-(methylsulfonyl)phenyl) propyl methyl carbonate;
(1R,2S)-2-(2,2-dichloroacetamido)-3-fluoro-1-(4-(methylsulfonyl)phenyl)propyl ethyl carbonate;
(1R,2S)-2-(2,2-dichloroacetamido)-3-fluoro-1-(4-(methylsulfonyl)phenyl)propyl propyl carbonate;

(1R,2S)-2-(2,2-dichloroacetamido)-3-fluoro-1-(4-(methylsulfonyl)phenyl)propyl isopropyl carbonate;

(1R,2S)-2-(2,2-dichloroacetamido)-3-fluoro-1-(4-(methylsulfonyl)phenyl)propyl isobutyl carbonate;

cyclopropylmethyl (1R,2S)-2-(2,2-dichloroacetamido)-3-fluoro-1-(4-(methylsulfonyl)phenyl)propyl carbonate;

(1R,2S)-2-(2,2-dichloroacetamido)-3-fluoro-1-(4-(methylsulfonyl)phenyl)propyl 3-methylbut-2-enyl carbonate;

(1R,2S)-2-(2,2-dichloroacetamido)-3-fluoro-1-(4-(methylsulfonyl)phenyl)propyl isopentyl carbonate;

(1R,2S)-2-(2,2-dichloroacetamido)-3-fluoro-1-(4-(methylsulfonyl)phenyl)propyl octyl carbonate;

(1R,2S)-2-(2,2-dichloroacetamido)-3-fluoro-1-(4-(methylsulfonyl)phenyl)propyl 2-(2-(2-methoxyethoxy)ethoxy)ethyl carbonate;

(1R,2S)-2-(2,2-dichloroacetamido)-3-fluoro-1-(4-fluoromethylsulfonyl)phenyl)propyl ethyl carbonate; and bis((1R,2S)-2-(2,2-dichloroacetamido)-3-fluoro-1-(4-(methylsulfonyl)phenyl)propyl) ethane-1,2-diyl dicarbonate.

12. A fenicol carbonate compound of Formula II,

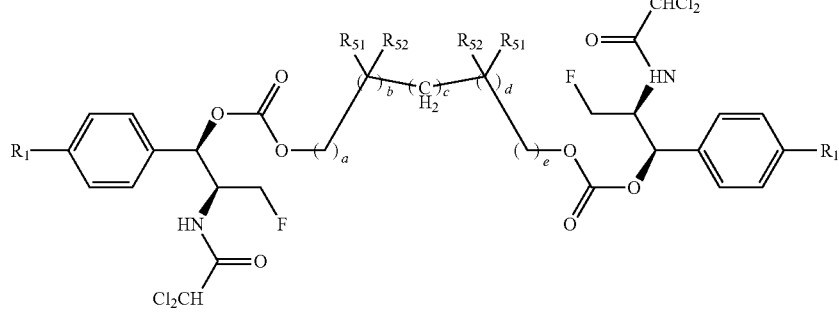

Formula II (1R,2S)-2-(2,2-dichloroacetamido)-3-fluoro-1-(4-(methylsulfonyl)phenyl)propyl pentan-3-yl carbonate;

cyclohexyl (1R,2S)-2-(2,2-dichloroacetamido)-3-fluoro-1-(4-(methylsulfonyl)phenyl)propyl carbonate;

(1R,2S)-2-(2,2-dichloroacetamido)-3-fluoro-1-(4-(methylsulfonyl)phenyl)propyl 2-methoxyethyl carbonate;

(1R,2S)-2-(2,2-dichloroacetamido)-3-fluoro-1-(4-(methylsulfonyl)phenyl)propyl 2-ethoxyethyl carbonate;

(1R,2S)-2-(2,2-dichloroacetamido)-3-fluoro-1-(4-(methylsulfonyl)phenyl)propyl-2-butoxyethyl carbonate;

benzyl (1R,2S)-2-(2,2-dichloroacetamido)-3-fluoro-1-(4-(methylsulfonyl)phenyl)propyl carbonate;

(1R,2S)-2-(2,2-dichloroacetamido)-3-fluoro-1-(4-(methylsulfonyl)phenyl)propyl 4-methylbenzyl carbonate;

(1R,2S)-2-(2,2-dichloroacetamido)-3-fluoro-1-(4-(methylsulfonyl)phenyl)propyl 4-methoxybenzyl carbonate;

(S)-ethyl 2-(1R,2S)-2-(2,2-dichloroacetamido)-3-fluoro-1-(4-(methylsulfonyl)phenyl)propoxy)carbonyloxy)propanoate;

(1R,2S)-2-(2,2-dichloroacetamido)-3-fluoro-1-(4-(methylsulfonyl)phenyl)propyl dodecyl carbonate;

(1R,2S)-2-(2,2-dichloroacetamido)-3-fluoro-1-(4-(methylsulfonyl)phenyl)propyl octadecyl carbonate;

(1R,2S)-2-(2,2-dichloroacetamido)-3-fluoro-1-(4-(methylsulfonyl)phenyl)propyl-(3R,S)-3,7-dimethyloct-6-enyl carbonate;

(1R,2S)-2-(2,2-dichloroacetamido)-3-fluoro-1-(4-(methylsulfonyl)phenyl)propyl 2-(2-methoxyethoxy)ethyl carbonate;

wherein $R_1$ is selected from the group consisting of

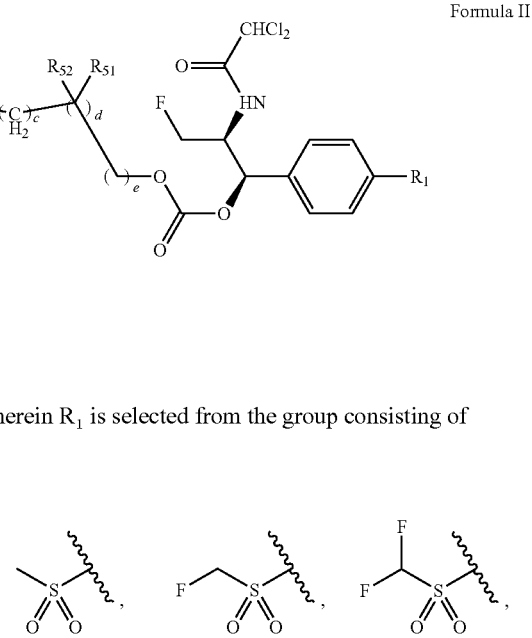

wherein a, c and e are integers that independently range in value from 0 through 4, b and d are integers that independently range in value from 0 through 2, provided that the sum of integers a, b, c, d and e range in value from 2 to 8, $R_{51}$ and $R_{52}$ are independently selected from the group consisting of H, methyl, hydroxyl, methoxy, and acetoxy.

13. The compound of claim 12 wherein the sum of a, b, c, d and e ranges in value from 2 through 4.

14. The compound of claim 12 where $R_1$ is

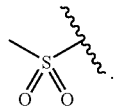

15. The compound of claim 12, having a structure selected from the group consisting of:

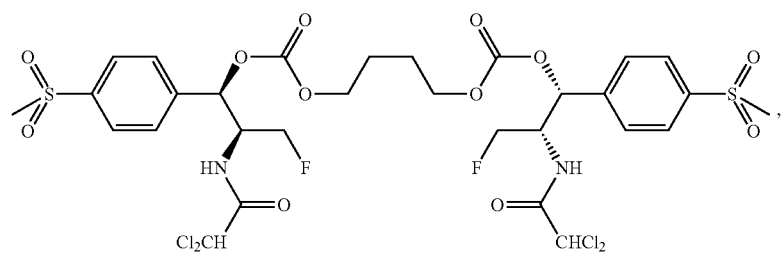
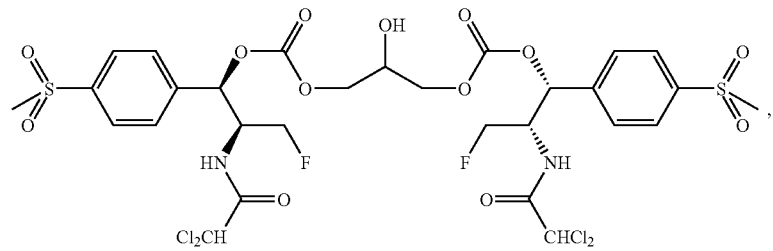
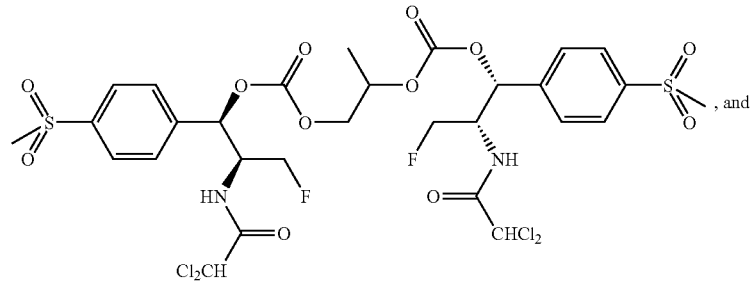
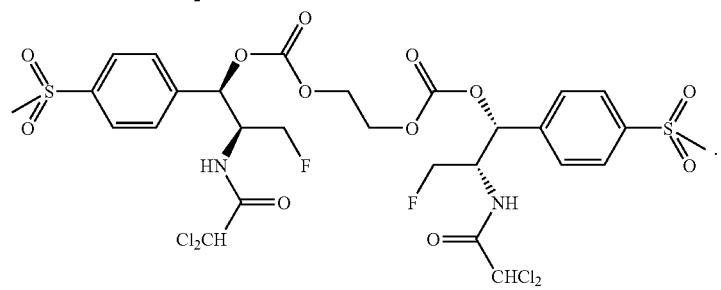
16. The compound of claim 1, having the following structure
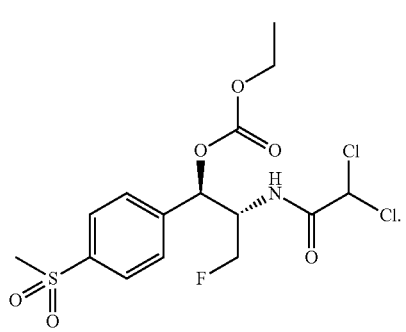
17. The compound of claim 15, having the following structure
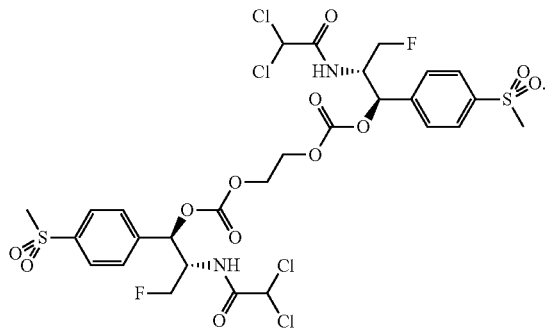
* * * * *